(12) United States Patent
Paul et al.

(10) Patent No.: US 7,326,204 B2
(45) Date of Patent: *Feb. 5, 2008

(54) BRUSH ELECTRODE AND METHOD FOR ABLATION

(75) Inventors: Saurav Paul, Minneapolis, MN (US);
Kedar Ravindra Belhe, Minnetonka, MN (US); Hong Cao, Shakopee, MN (US); Chou Thao, Brooklyn Park, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/808,919

(22) Filed: Mar. 24, 2004

(65) Prior Publication Data

US 2005/0159739 A1    Jul. 21, 2005

Related U.S. Application Data

(60) Provisional application No. 60/537,092, filed on Jan. 16, 2004.

(51) Int. Cl.
*A61B 18/18* (2006.01)
(52) U.S. Cl. ...................................................... 606/41
(58) Field of Classification Search .............. 606/27–52
See application file for complete search history.

(56) References Cited

U.S. PATENT DOCUMENTS

| | | | |
|---|---|---|---|
| 4,358,699 A * | 11/1982 | Wilsdorf | 310/251 |
| 4,415,635 A | 11/1983 | Wilsdorf et al. | |
| 5,676,693 A | 10/1997 | LaFontaine | |
| 6,015,407 A | 1/2000 | Rieb et al. | |
| 6,168,594 B1 | 1/2001 | LaFontaine et al. | |
| 6,402,745 B1 | 6/2002 | Wilk | |
| 6,780,180 B1 * | 8/2004 | Goble et al. | 606/41 |
| 2001/0024735 A1 | 9/2001 | Kuhlmann-Wilsdorf et al. | |

\* cited by examiner

*Primary Examiner*—Michael Peffley
*Assistant Examiner*—Pete Vrettakos
(74) *Attorney, Agent, or Firm*—Heimbecher & Assoc., LLC

(57) ABSTRACT

A brush electrode and a method for using the brush electrode for tissue ablation are disclosed. The brush electrode comprises a plurality of flexible filaments or bristles for applying ablative energy (e.g., RF energy) to target tissue during the formation of spot or continuous linear lesions. Interstitial spaces are defined among the filaments of the brush electrode, and the interstitial spaces are adapted to direct conductive or nonconductive fluid, when present, toward the distal ends of the brush filaments. The brush electrode facilitates electrode-tissue contact in target tissue having flat or contoured surfaces. The flexible filaments may be selectively trimmed to give a desired tip configuration or a desired standoff distance between the tissue and the conductive filaments in the brush electrode. Also, the filaments may be grouped into clusters. A shielded-tip brush electrode, including a flexible boot, is also disclosed.

18 Claims, 18 Drawing Sheets

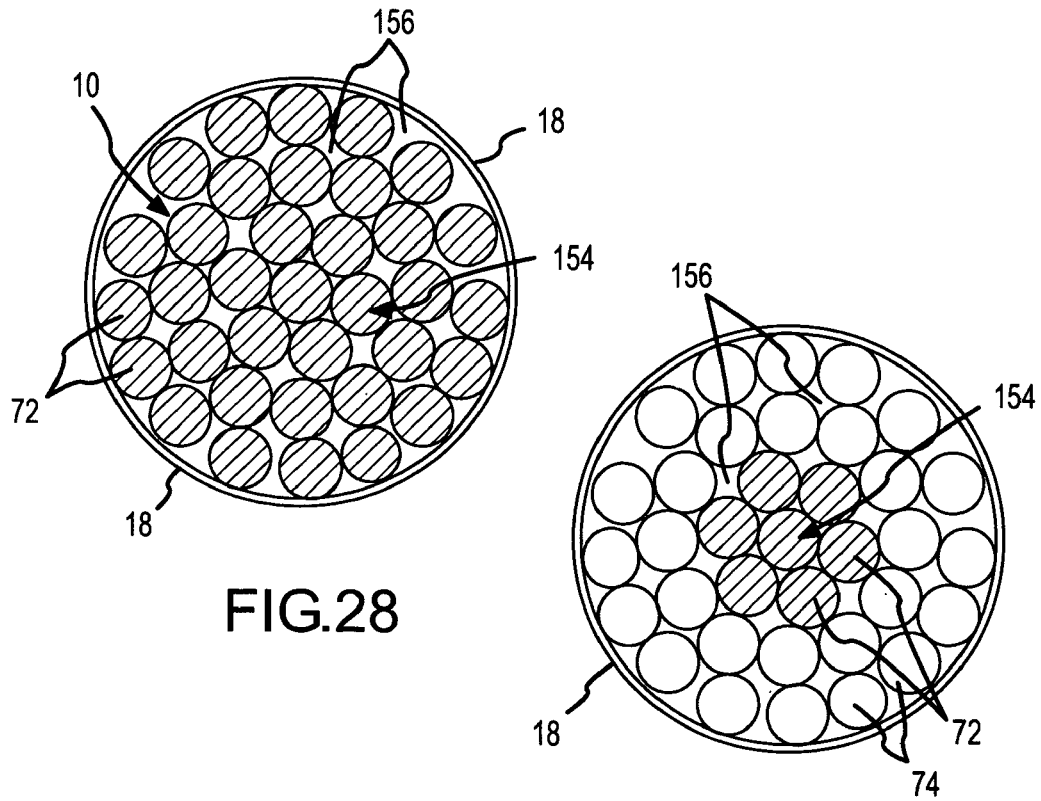
FIG.28
FIG.29
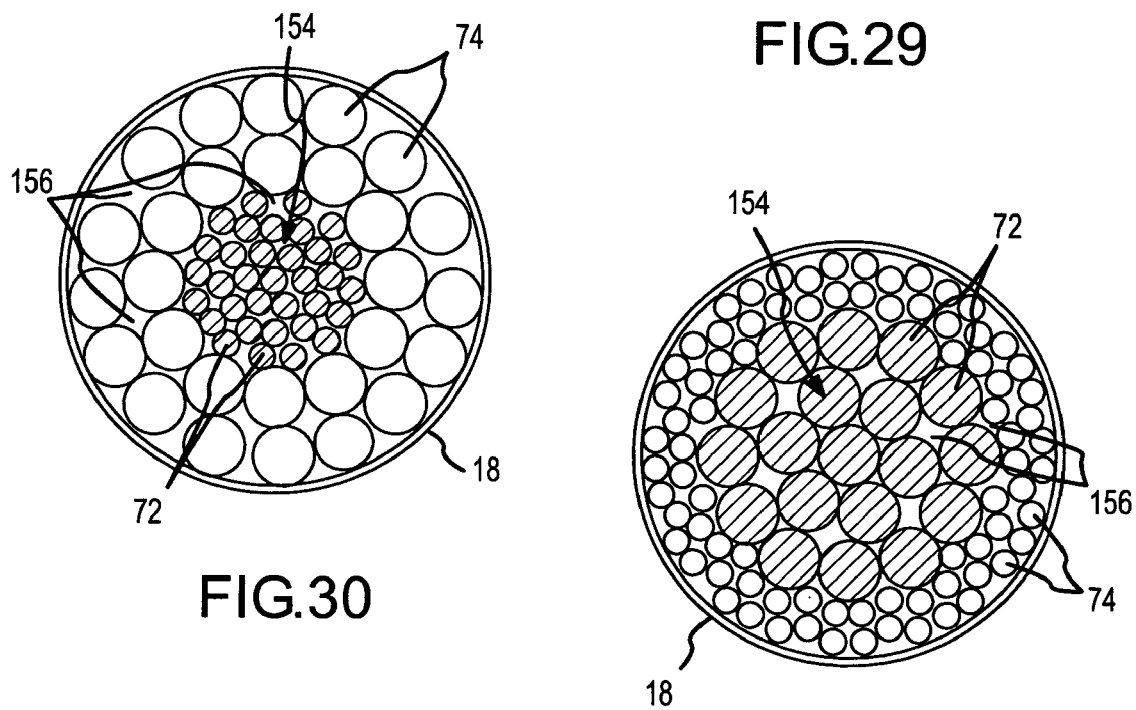
FIG.30
FIG.31

BRUSH ELECTRODE AND METHOD FOR ABLATION

This application claims priority pursuant to U.S. Provisional Application No. 60/537,092, filed 16 Jan. 2004 (the '092 application). The '092 application is hereby incorporated by reference as though fully set forth herein. This application is related to: U.S. application Ser. No. 10/856,925 (the '925 application) filed May 27, 2004, which is a continuation-in-part of this application and claims priority pursuant to 35 U.S.C. §119(e) to the '092 application; U.S. application Ser. No. 10/856,926 (the '926 application) filed May 27, 2004, which is also a continuation-in-part of this application and also claims priority to the '092 application; and U.S. application Ser. No. 11/190,724 (the '724 application) filed, Jul. 27, 2005, which is a continuation-in-part of each of the '925, '926, and the present application and also claims the benefit of priority to the '092 application.

BACKGROUND OF THE INVENTION a. Field of the Invention

The instant invention is directed toward a brush electrode and a method for using the brush electrode for tissue ablation. In particular, the brush electrode of the present invention comprises a plurality of flexible filaments or bristles for applying ablative energy (e.g., RF energy) to target tissue during the formation of spot or continuous linear lesions.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable atrial fibrillations may be lessened or eliminated. "Sufficiently deep" lesions means transmural lesions in some cardiac applications.

Several difficulties may be encountered, however, when attempting to form adequately-deep lesions at specific locations using some existing ablation electrodes. For example, when forming lesions with RF energy, high temperature gradients are often encountered in the vicinity of the electrode. At the edges of some existing electrodes are regions of very high current density, leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There two types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue. Active temperature control may help, but the placement of thermocouples, for example, is tricky and setting the RF generator for a certain temperature becomes an empirical exercise as actual tissue temperatures are generally different from those recorded next to the electrode due to factors such as convection and catheter design.

Another difficulty encountered with existing ablation electrodes is how to ensure adequate tissue contact. Current techniques for creating continuous linear lesions in endocardial applications include, for example, dragging a conventional catheter on the tissue, using an array electrode, or using pre-formed electrodes. All of these devices comprise rigid electrodes that do not always conform to the tissue surface, especially when sharp gradients and undulations are present, such as at the ostium of the pulmonary vein in the left atrium and the isthmus of the right atrium. Consequently, continuous linear lesions are difficult to achieve. When forming lesions in a heart, the beating of the heart further complicates matters, making it difficult to keep adequate contact between the electrode and the tissue for a sufficient length of time to form a desired lesion. With a rigid electrode, it can be quite difficult to maintain sufficient contact pressure until an adequate lesion has been formed. This problem is exacerbated on contoured or trabeculated surfaces. If the contact between the electrode and the tissue cannot be properly maintained, a quality lesion is unlikely to be formed.

Catheters based upon a virtual electrode may address some of the difficulties, but these catheters often require high flow rates of conductive fluid (e.g., typically around 70 milliliters per minute) to maintain effective cooling for high-power RF applications. The introduction of a large amount of conductive fluid into a patient's bloodstream may have detrimental effects on the patient.

Thus, there remains a need for an ablation catheter that address these issues with the existing designs and that permits the formation of uniform, transmural spot and continuous linear lesions on smooth or contoured surfaces.

BRIEF SUMMARY OF THE INVENTION

It is desirable to be able to form adequately-deep spot or continuous linear lesions in tissue while reducing the formation of undesirable coagulum and charring of the surface tissue, while applying a reasonable amount of RF energy, while mitigating electrode-tissue contact problems, and/or while reducing the amount of conductive fluid (e.g., isotonic saline) possibly entering a patient's bloodstream during the procedure. The present invention is an improved ablation electrode.

In one form, the present invention comprises a wet-brush electrode that facilitates electrode-tissue contact in target tissue having contoured surfaces. The wet-brush electrode comprises a plurality of flexible filaments adapted to transfer ablative energy to target tissue, the flexible filaments having longitudinal axes and defining interstitial spaces among the plurality of filaments, wherein the interstitial spaces are adapted to direct conductive fluid predominantly parallel to the filament longitudinal axes. This wet-brush electrode also comprises a primary conductor operatively connected to, and adapted to transfer ablative energy to, the plurality of flexible filaments; and a fluid-delivery means adapted to deliver conductive fluid to the interstitial spaces.

In another form, the present invention comprises a catheter for tissue ablation. The catheter comprises an outer sheath having a distal end and a brush electrode, the brush electrode comprising (a) a plurality of flexible filaments adapted to transfer ablative energy to target tissue during lesion formation, wherein the flexible filaments extend from the distal end of the outer sheath; and (b) a primary conductor in electrical contact with the plurality of filaments. Although the brush electrode may be merely frictionally engaged with the distal end of the outer sheath, the catheter may also comprises an attachment means for physically securing the brush electrode to the distal end of the outer sheath. The filaments may be conductive filaments and/or nonconductive filaments, and the filaments may have nonuniform cross-sectional configurations (e.g., the may be tapered). Further, nonconductive tips may be present at the distal ends of at least some of the flexible filaments.

In yet another form, the present invention comprises a catheter for ablating tissue inside a human body. The catheter comprises an outer sheath having a distal end; a conforming electrode adapted to apply ablative energy to target tissue, the conforming electrode comprises an embedded portion and an exposed portion, wherein the exposed portion has a distal end, wherein a working surface is present at the distal end of the exposed portion, and wherein the exposed portion extends from the distal end of the outer sheath; and a primary conductor in direct electrical contact with the conforming electrode and adapted to carry ablative energy from an energy source to the conforming electrode. The conforming electrode may comprise a dry or wetted brush electrode having a plurality of flexible filaments. The flexible filaments may be trimmed to give a desired tip configuration or a desired standoff distance between the tissue and the conductive filaments in the brush electrode. Also, the filaments may be grouped into clusters.

In still another form, the present invention comprises a catheter for tissue ablation, wherein the catheter includes a shielded-tip brush electrode. In particular, the catheter comprises an outer sheath having a distal end; a shielded-tip brush electrode at the distal end of the outer sheath, the shielded-tip brush electrode comprising (a) a bundle of filaments adapted to transfer ablative energy to target tissue during the formation of a lesion, wherein the bundle of filaments extend from the distal end of the outer sheath, and wherein the bundle of filaments has an outer surface; and (b) a primary conductor having an uninsulated portion, wherein the uninsulated portion is in electrical contact with the plurality of filaments. Attachment means may be present to secure the shielded-tip brush electrode to the distal end of the outer sheath.

In another form, the present invention comprises a catheter having an outer sheath with a distal end; an inner sheath with a distal end; an annular channel defined between the outer sheath and the inner sheath, wherein the annular channel is adapted to carry fluid; a mechanical interface supported at least in part by the distal end of the inner sheath; a flexible electrode adapted to apply ablative energy to target tissue, wherein the flexible electrode is supported by the mechanical interface, wherein the flexible electrode comprises an embedded portion and an exposed portion, and wherein the exposed portion extends from the distal end of the outer sheath and comprises a working surface; a primary conductor adapted to carry ablative energy from an energy source to the flexible electrode, wherein the primary conductor comprises an uninsulated portion in electrical contact with the flexible electrode; and a flexible boot at the distal end of the outer sheath, the flexible boot defining an annular fluid jacket around a booted portion of the flexible electrode, wherein the booted portion comprises at least a portion of the exposed portion of the flexible electrode, and wherein the annular fluid jacket is adapted to carry fluid that is in fluid communication with the annular channel.

The present invention also comprises a method of ablating tissue inside a human body using a flexible brush electrode affixed at a distal end of an outer sheath of a catheter. The method comprising the steps of placing an exposed portion of the brush electrode adjacent to tissue to be treated; applying ablative energy to the exposed portion of the brush electrode; and forming a lesion in the tissue via coagulation necrosis.

In each of the brush electrode embodiments described above, the filaments comprising the brush have interstitial gaps between them. The interstitial gaps are adapted to direct fluid, when present, toward the tissue being treated.

In each of the brush electrodes described above, a secondary lead may also be present and may have a device (e.g., a thermocouple, a pressure sensor, and an ultrasound sensor) operatively connected with it.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 28-35 depict different cross-sectional configurations for brush electrodes according to the present invention.

DETAILED DESCRIPTION OF THE INVENTION

Several embodiments of a brush electrode 10 according to the present invention are depicted in the figures. As described further below, the brush electrode of the present invention provides a number of advantages, including, for example, the ability to form deep lesions in tissue while reducing the formation of undesirable coagulum and charring of the surface tissue, while applying a reasonable amount of RF energy, while mitigating electrode-tissue contact problems, and/or while reducing the amount of conductive fluid (e.g., saline) possibly entering a patient's bloodstream during the procedure. The present invention facilitates the formation of a deep lesion in a shorter period of time than required by other ablation devices, and it provides the ability to create lesions in highly perfused tissue or in fluid-rich environments. The brush electrode 10 facilitates enhanced tissue contact in difficult environments (e.g., during ablation of a contoured or trabeculated surface inside a beating heart), whether creating a spot lesion 12 (e.g., FIG. 38) or a continuous linear lesion 14 (e.g., FIG. 39), by readily conforming to surface contours.

Figure 1:
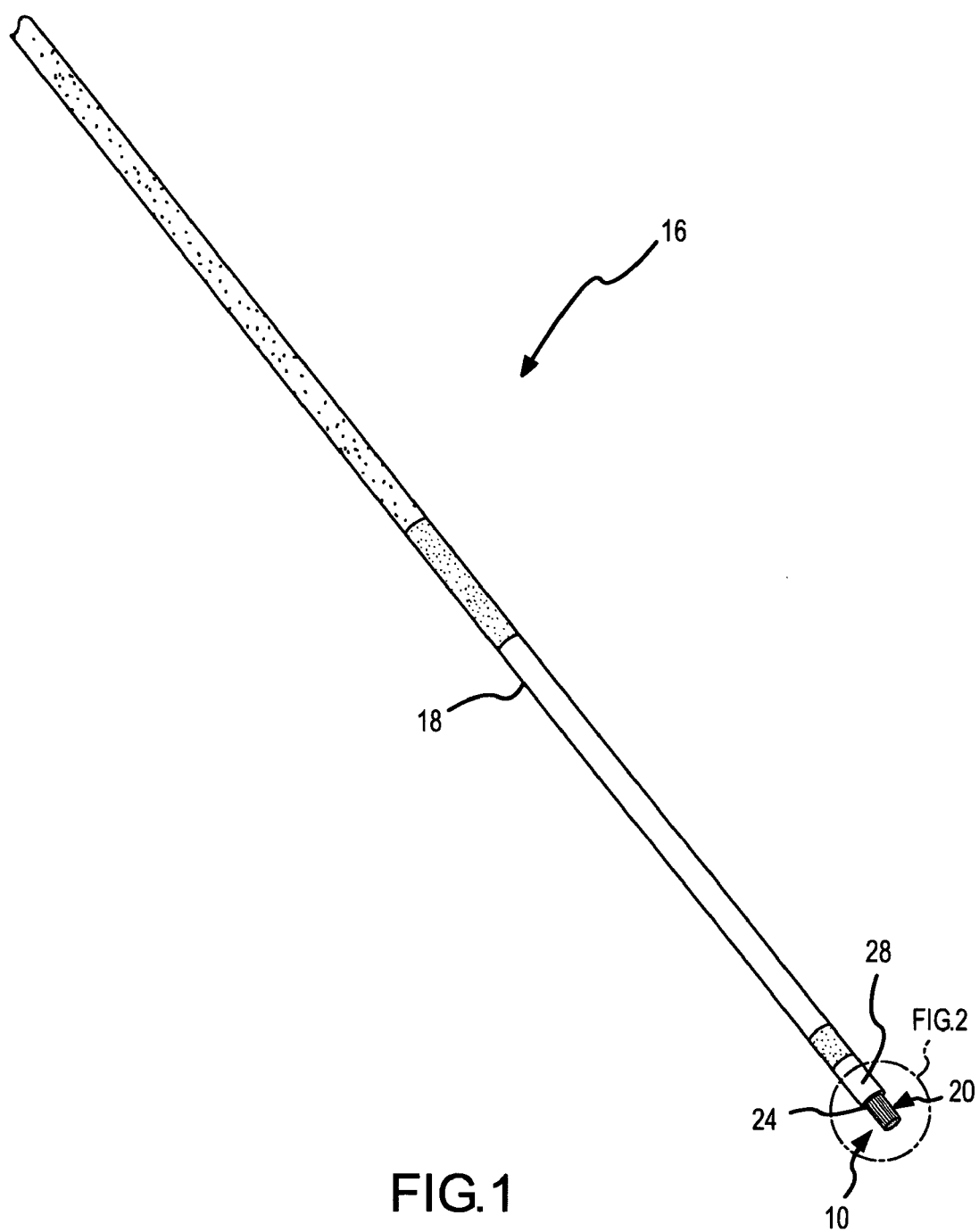
FIG. 1 is an isometric view of one embodiment of a catheter having a brush electrode according to the present invention, and depicts the filaments comprising the brush electrode extending from a distal end of an outer sheath.

FIG. 1 is an isometric view of one embodiment of a catheter 16 having a brush electrode 10 according to the present invention. As depicted in this figure, the catheter comprises a catheter shaft with an outer sheath 18. In the embodiment depicted in FIG. 1, the outer sheath is formed from sections of different material (e.g., in the embodiment depicted FIG. 1, five different sections comprise the outer sheath). These sections of different material enable the catheter 16 to have, for example, different mechanical properties (e.g., flexibility) at different locations along the catheter shaft. The outer sheath 18 may or may not comprise these sections of different material depending upon the intended application for the catheter. Although the outer sheath 18 depicted in FIG. 1 has a circular cross section, the cross-section of the outer sheath may be other than circular.

As also shown in FIG. 1, the brush electrode 10, which comprises an exposed portion 20 and an embedded portion 22 (see, e.g., FIG. 5), is present at a distal end 24 of the outer sheath 18. In particular, at the distal end of the outer sheath, the exposed portion 20 of the brush electrode 10, comprising a plurality of filaments 26, may be seen (see, e.g., FIG. 2). The exposed portion of the brush electrode may project a few millimeters from the distal end of the outer sheath. The distance that the exposed portion of the brush electrode extends from the distal end of the outer sheath varies depending upon a number of factors including the composition of the filaments comprising the brush and the particular area to be treated with the brush electrode 10. The distal end 24 of the outer sheath 18 may include a conductive or nonconductive base 28. As explained further below, the flexible brush electrode provides enhanced tissue contact, particularly for use on contoured or trabeculated surfaces.

Figure 2:
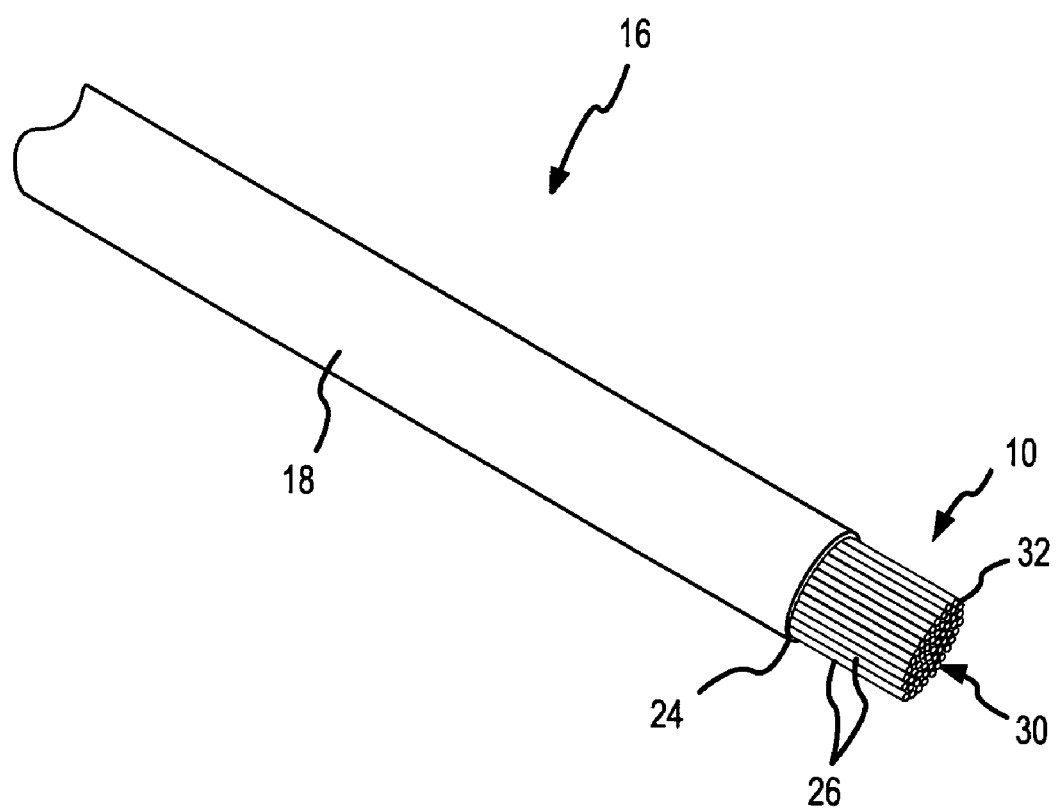
FIG. 2 is an enlarged view of the circled region of FIG. 1.

FIG. 2 is an enlarge view of the circled region of FIG. 1. As clearly shown in FIG. 2, the brush electrode 10 according to this embodiment has a relatively flat working surface 30 at the distal end 32 of the brush electrode 10. In other words, in this depicted embodiment, all of the filaments 26 comprising the brush electrode 10 extend approximately the same distance from the distal end 24 of the outer sheath 18. Thus, the brush tip provides a relatively flat working surface 30 comprising the longitudinal ends of the filaments. The outer sheath of the catheter provides mechanical support for the filaments and may also provide electrical shielding. As explained further below, the brush electrode comprises a bundle of bristles or filaments that each may be constructed from a variety of different materials, including nonconductive materials, semi-conductive materials, and conductive materials. For example, the filaments may be formed from metal fibers, metal plated fibers, carbon-compound fibers, and other materials. Very thin, carbon fibers may be used, or relatively thicker but less conductive Thunderon® acrylic fibers may be used for the brush electrode filaments. Thunderon® is manufactured by Nihon Sanmo Dyeing Company Ltd. of Kyoto, Japan. Nylon fibers coated with conductive material may also be used. Filaments 26 constructed from metal plated fibers, like coated nylon fibers, may comprise flattened areas around their outer surfaces, resulting in the filaments having noncircular cross-sectional shapes. The brush filaments may be insulated from each other, or they may be in electrical contact with each other. As explained further below, conductive or nonconductive fluids 34 may flow within the filaments themselves (see, e.g., FIG. 36) or along the outer surface of the filaments (see, e.g., FIG. 5).

Figure 3:
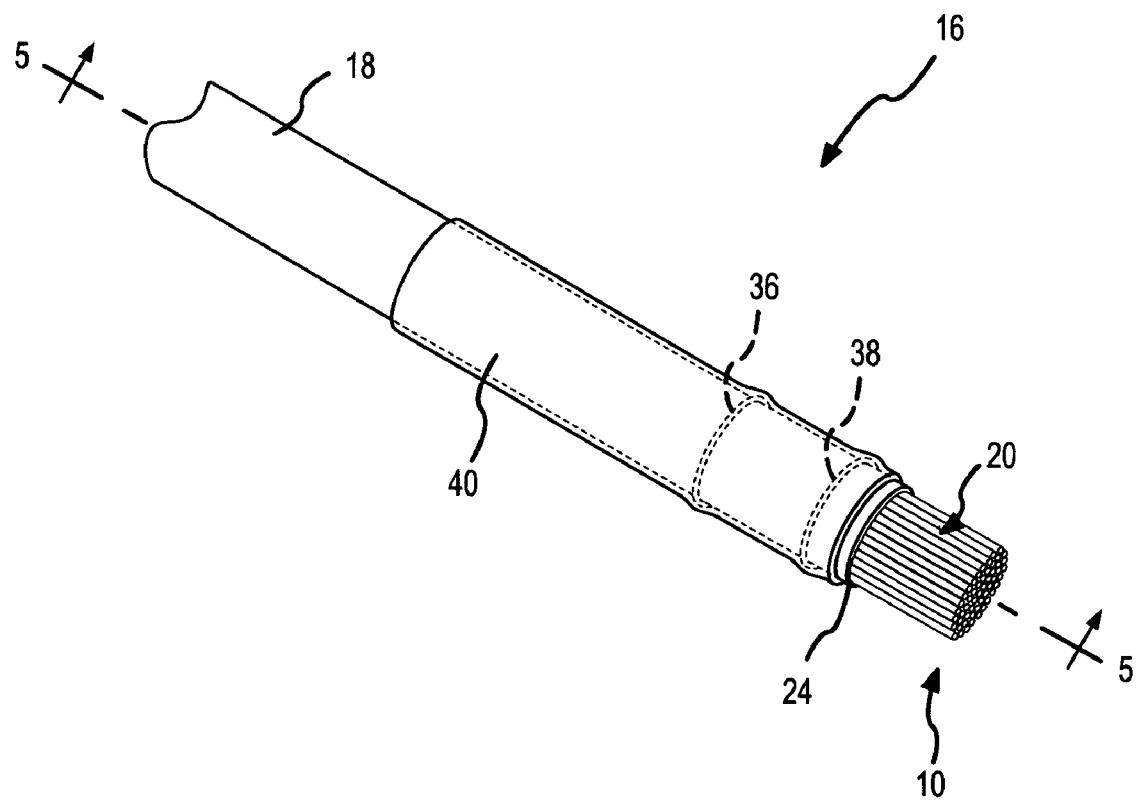
FIG. 3 is similar to FIG. 2, but depicts an alternative embodiment where the brush electrode is secured at the distal end of the outer sheath by at least one suture that is covered by a section of shrink tube.
Figure 4:
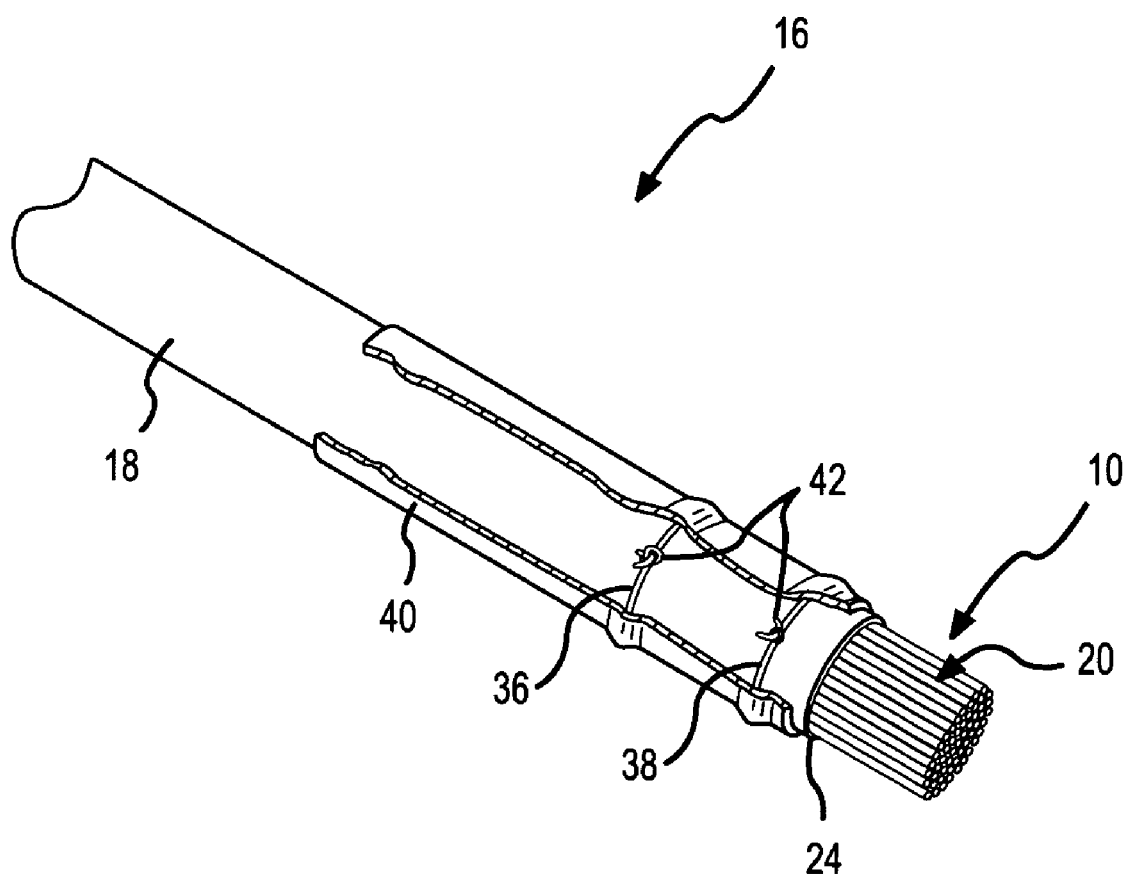
FIG. 4 is similar to FIG. 3, but a portion of the shrink tube has been broken away to reveal two sutures through the outer sheath.
Figure 5:
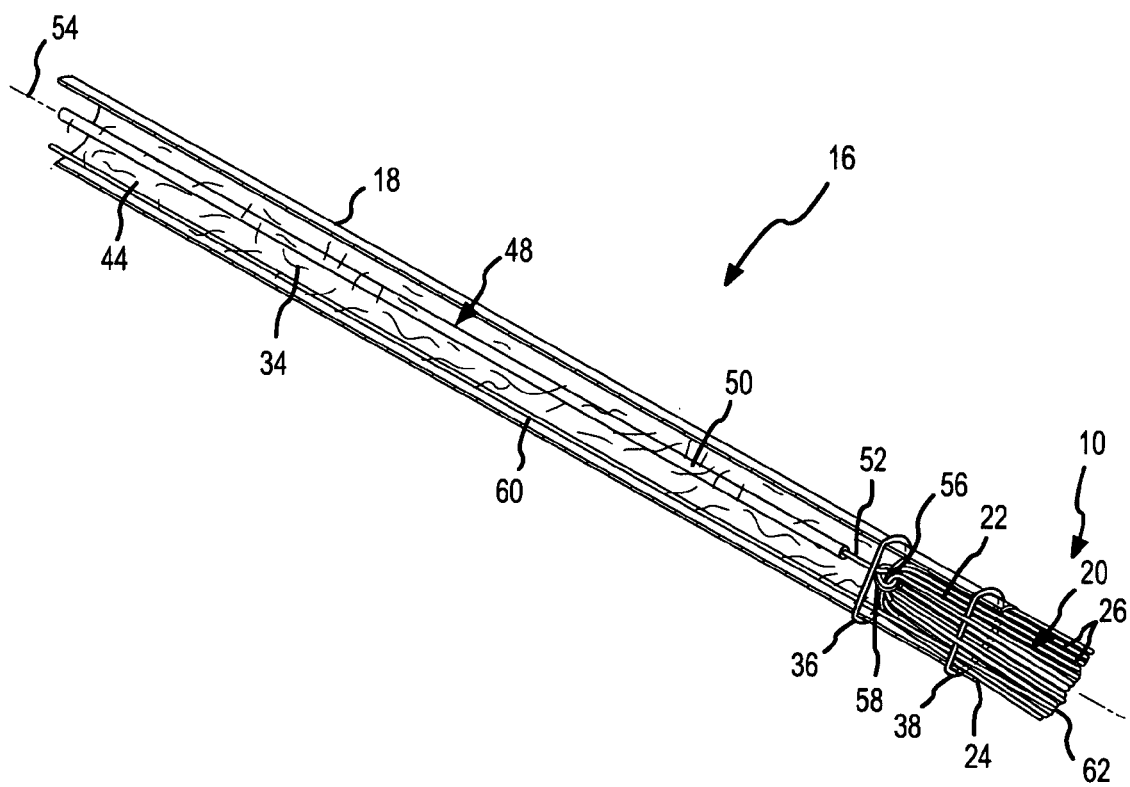
FIG. 5 is an isometric, cross-sectional view of the catheter depicted in FIGS. 3 and 4, taken along line 5-5 of FIG. 3, revealing a primary conductor making electrical contact with the filaments comprising the brush electrode, and depicting a secondary lead (e.g., for a thermocouple) extending adjacent to the primary conductor and becoming embedded within the brush filaments.

Once the distance that the filaments extend from the distal end 24 of the other sheath 18 is set to a desired length, the bundle of filaments comprising the brush electrode 10 may be fixed to the outer sheath 18. FIGS. 3-5 depict one technique for fixing or anchoring the brush electrode 10 relative to the outer sheath using sutures. In FIG. 3, a rearward suture 36 and a forward suture 38 are shown in phantom under a section of shrink tube 40 surrounding the outer surface of the outer sheath 18. The shrink tube protects the sutures and makes it easier to insert the catheter by mitigating possible snags that may occur due to the presence of the sutures. FIG. 4 is similar to FIG. 3, but depicts a portion of the shrink tube 40 broken away to reveal a portion of the two sutures 36, 38. The suture knots 42 are clearly visible in FIG. 4.

FIG. 5 is an isometric, cross-sectional view of the catheter 16 depicted in FIGS. 3 and 4, taken along line 5-5 of FIG. 3. In FIG. 5, it is apparent that the rearward suture 36 may be used to set the depth that the brush electrode 10 may be inserted into the distal end 24 of the outer sheath 18. In this figure, the forward suture 38 pierces the filaments 26 comprising the embedded portion 22 of the brush electrode 10 and thereby help prevent movement of the brush electrode relative to the outer sheath of the catheter. In the embodiment depicted in FIG. 5, conductive fluid 34 is shown flowing through a lumen 44 of the outer sheath (depicted as a single, embedded channel) from a fluid source (not shown) to the brush electrode 10. When the conductive fluid 34 flows through the brush electrode, it creates a wet-brush electrode in which impinging jets of fluid traveling interstitially impact the tissue 46 (see, e.g., FIGS. 38 and 39) at the tissue-electrode interface, which makes it easier to control temperature rises at the interface. Wet-brush electrodes are discussed further below. In an alternative embodiment, the lumen 44 depicted in FIG. 5 may comprise a plurality of separate lumen.

Figure 7:
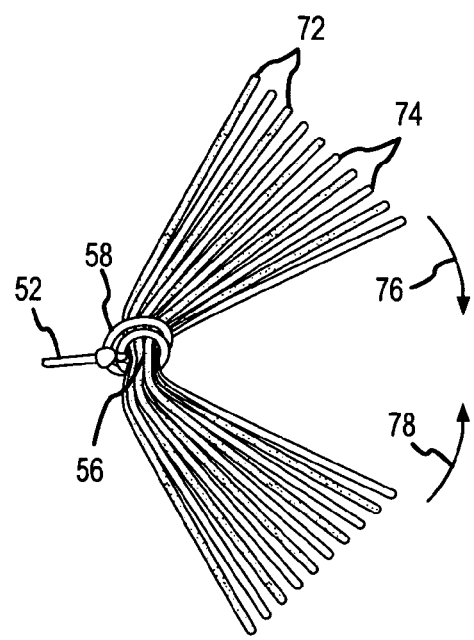

FIG. 5 also clearly depicts a primary conductor 48 having an insulated portion 50 and an uninsulated portion 52. The primary conductor carries ablative energy (e.g., RF current) from an energy source (not shown) to the brush electrode 10. As depicted in FIG. 5, the primary conductor 48 extends within the fluid-carrying lumen 44 of the catheter, along a longitudinal axis 54 of the catheter 16. The primary conductor may comprise, for example, insulated copper wire with an uninsulated portion in electrical contact with the brush electrode. In this embodiment, the uninsulated portion 52 of the primary conductor is looped or noosed around the filaments comprising the brush electrode at a connection point 56 (FIG. 7). At the loop or noose 58, ablative energy is transferred from the primary conductor to the conductive filaments comprising part of the brush electrode 10. In this embodiment, the uninsulated portion 52 of the primary conductor 48 is connected to the embedded portion 22 of the brush electrode 10 so that the connection between the primary conductor and the brush electrode is protected within the outer sheath 18 of the catheter 16.

Also clearly visible in FIG. 5 is an embedded or secondary lead 60, which extends substantially parallel to the primary conductor 48. A distal end 62 of the secondary lead 60 becomes embedded with the filaments 26 comprising the brush electrode 10. As discussed further below in connection with, for example, FIG. 37, the secondary lead 60, when present, may be operatively connected to some type of sensor embedded in the brush electrode (e.g., a thermal sensor 64, an ultrasound sensor 66, or a pressure sensor 68). The brush electrode depicted in FIG. 5 acts as a surface-cooled electrode 10.

Figure 6:
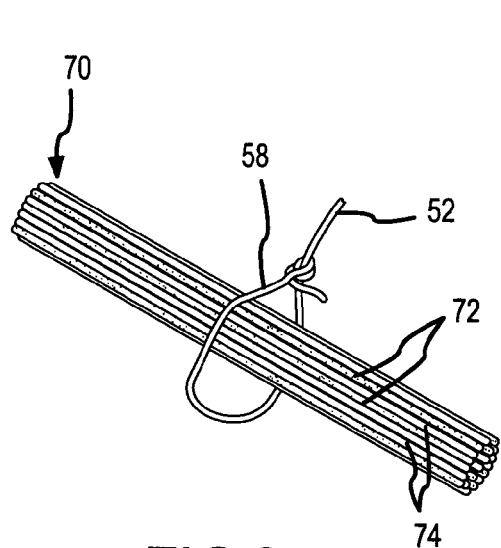
FIGS. 6 and 7 depict steps that may be used to form the brush electrode depicted in, for example, FIG. 5.

FIGS. 6 and 7 depict possible steps for forming the brush electrode 10 depicted in FIGS. 1-5. In FIG. 6, a bundle 70 of conductive filaments 72 and nonconductive filaments 74 is being formed by using the uninsulated portion 52 of the primary conductor 48 to bind or tie together the filaments. In FIG. 6, the uninsulated portion has been noosed around the bundle of filaments 70, but has not been tightened or snugged against the bundle. In FIG. 7, the uninsulated portion 52 of the primary conductor has been snuggly noosed around the connection point 56 at approximately the mid-section of the bundle of filaments that will ultimately form the brush electrode 10. The conductive filaments 72 and the nonconductive filaments 74 are then bent around the connection point 56 in the direction of the arrows 76, 78 depicted in FIG. 7. Once the filaments are folded upon themselves about the connection point 56, they are inserted into the distal end 24 of the outer sheath 18 and positioned relative to the distal end 24 of the outer sheath 18 so that the desired amount of the filaments extends from the distal end of the sheath and comprises the exposed portion 20 of the brush electrode 10. The ends of the filaments may then be trimmed, if desired, to create a desired shape for the working surface 30 at the distal end 32 of the brush electrode 10 (see, e.g., FIGS. 11-14).

Figure 8:
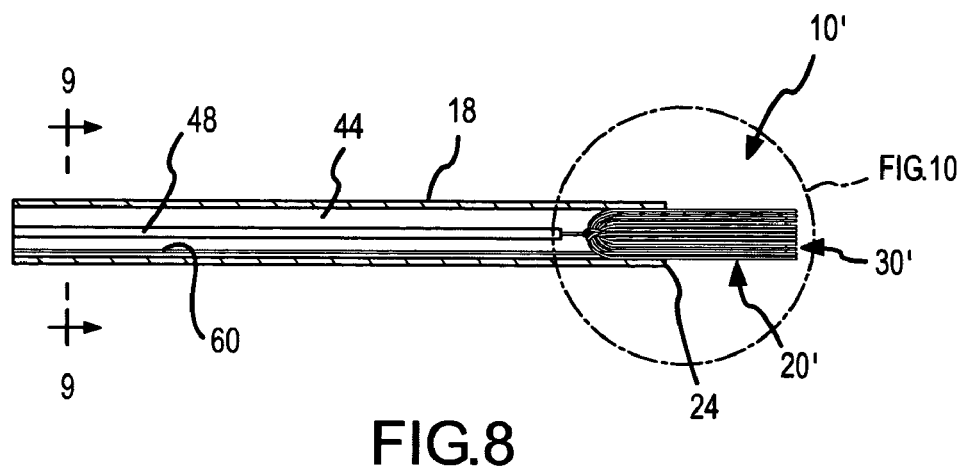
FIG. 8 is similar to FIG. 5, but is a cross-sectional view of an alternative embodiment of the brush electrode, wherein conductive filaments are interspersed among relatively longer nonconductive filaments.
Figure 9:
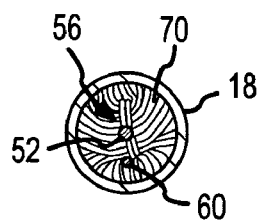
FIG. 9 is a cross-sectional view taken along line 9-9 of FIG. 8.
Figure 10:
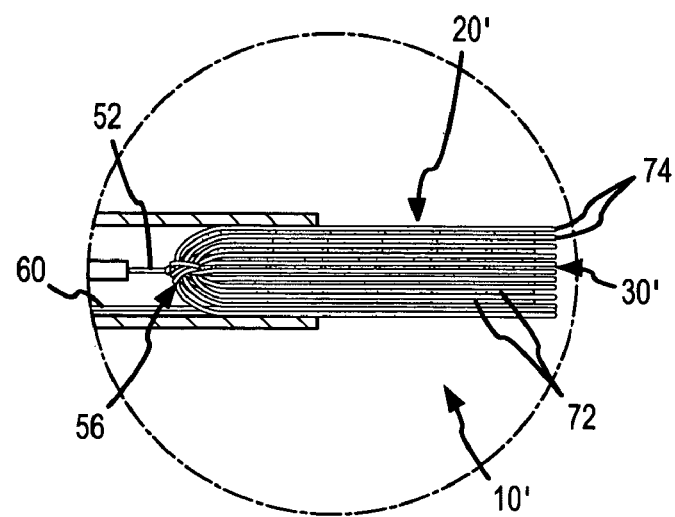
FIG. 10 is an enlarged view of the circled region of FIG. 8.

FIGS. 8, 9, and 10 depict an alternative embodiment of the brush electrode. This standoff brush electrode 10' includes an exposed portion 20' with a working surface 30' wherein the longitudinal ends of the conductive filaments 72 are not flush with the longitudinal ends of the nonconductive filaments 74. As shown to better advantage in FIG. 10, which is an enlarged view of the circled region of FIG. 8, in this alternative embodiment of the brush electrode, the conductive filaments 72 are interspersed among relatively longer nonconductive filaments 74. The relatively longer nonconductive filaments prevent the conductive filaments from directly touching the tissue 46 (see, e.g., FIG. 40) when the working surface 30' of the brush electrode is placed normal to the tissue being treated. With this brush configuration and substantially perpendicular orientation of the brush working surface 30' relative to the tissue being treated, the brush electrode acts as a virtual electrode. If the perpendicular orientation can be maintained, there is no direct contact between the conductive filaments and the tissue, and the conductive fluid 34 (see FIG. 5) flowing through the lumen 44 of the outer sheath 18 makes the electrical contact at the brush-tissue interface. Although FIGS. 8 and 10 depict each of the conductive filaments 72 as being shorter than each of the nonconductive filaments 74, the electrical characteristics of the brush electrode may be adjusted by having some conductive filaments that extend to the working surface at the tip of the brush electrode, if desired.

FIG. 9 is a cross-sectional view taken along line 9-9 of FIG. 8 and clearly depicts the bundled filaments 70 at the connection point 56 between the filaments and the uninsulated portion 52 of the primary conductor. The secondary lead 60 is also visible in FIG. 9. In this embodiment, it is possible to adjust the fluid and electrical contact at the brush-tissue interface through appropriate selection of the conductive and nonconductive filaments. Since this configuration of the brush electrode performs most effectively when placed normal or perpendicular to the tissue, a relatively short exposed portion 20' for the brush electrode 10' may be desirable with relatively stiff filaments (e.g., Thunderon® filaments).

Figure 11:
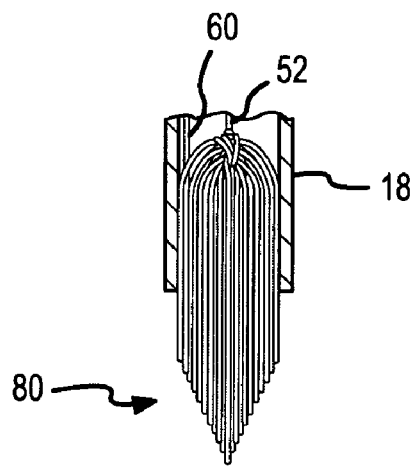
FIGS. 11-14 depict alternative shapes for the filaments comprising the tip of the brush electrode.
Figure 12:
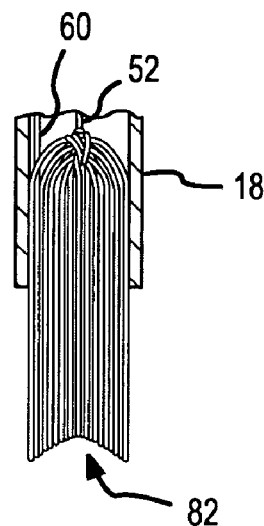
Figure 13:
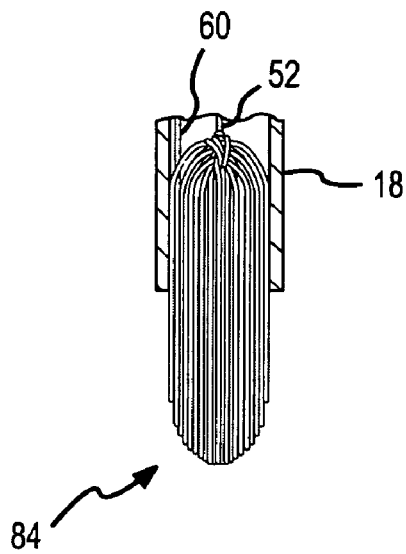
Figure 14:
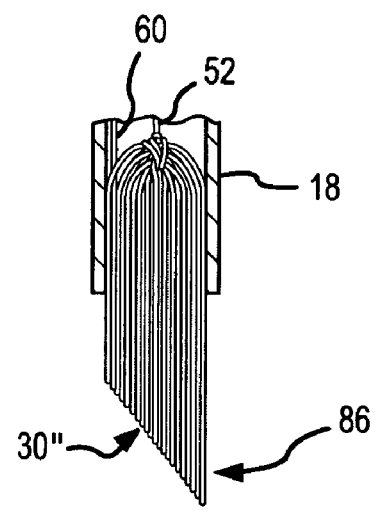

FIGS. 11-14 depict alternative shapes for the filaments 26 comprising the tip of the brush electrode. The various tip configurations may provide advantages for special applications of brush electrodes. FIG. 11 depicts a blade-shaped distal tip 80 creating a line of contact with the longest filaments of the brush electrode. As depicted in FIG. 11, the line of contact at the most distal end of the brush electrode extends perpendicularly into the page. In FIG. 12, the working surface of the electrode tip has a concave portion or channel 82. The concave-tip embodiment depicted in FIG. 12 is beneficial for wrap-around applications and provides advantages when ablating curved surfaces like the outer surface of a blood vessel. FIG. 13 depicts a convex, trough-shaped tip 84. This particular configuration is beneficial, for example, when reaching into troughs or depressions on a contoured surface. The distal tip could also be domed or hemispherical rather than having the trough-shaped contact surface shown in FIG. 13. In FIG. 14, the brush electrode has a wedge-shaped tip 86. The wedge-shaped tip facilitates angular placement and increases the area of the working surface 30". The distal tip could also be conical (not shown), coming nearly to a point at the most distal end of the brush electrode, with its longest filaments proximal to the longitudinal axis 54 of the catheter 16 (see FIG. 5). This latter configuration may be advantageous for point applications of ablative energy. The brush electrodes are depicted in many of the drawings with circular cross sections, but may have different cross-sectional configurations.

Figure 15:
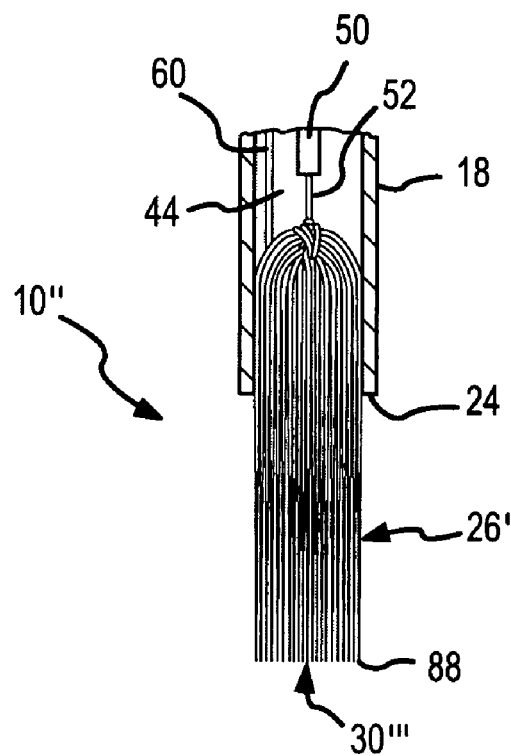
FIG. 15 depicts an alternative embodiment of the filaments comprising the brush electrode, wherein the individual filaments gradually taper toward their distal ends.

FIG. 15 depicts an example of a brush electrode 10''' having continuously varying conductivity along the longitudinal axes of the filaments. In particular, the brush electrode comprises tapered filaments 26'. In this alternative embodiment, at least a portion of the individual filaments 26' comprising the brush electrode 10''' gradually taper toward their distal or free ends 88. In other words, at the distal end 24 of the outer sheath 18, the filaments 26' have larger cross-sectional areas than they have at their distal ends 88, adjacent to the working surface 30''' of the brush electrode 10'''. The filaments 26' are thus more conductive adjacent to the distal end of the outer sheath and less conductive at the distal ends of the filaments. Since the filaments are more conductive adjacent to the distal end of the outer sheath, this minimizes current flow to the less conductive fluid wetting the brush from the lumen of the outer sheath. When less of the ablative energy flows into the conductive fluid adjacent to the distal end of the outer sheath, this minimizes the energy transfer into the conductive fluid and the concomitant heating of the conductive fluid before it contacts the surface of the tissue. At the distal ends 88 of the filaments 26' depicted in FIG. 15, the conductivity of the filaments may be matched to the conductivity of the fluid to create a relatively uniform electric field at the brush-tissue interface.

The taper depicted in FIG. 15 could be an inverse taper, which may be advantageous for certain applications. It should be noted that, in order to vary the conductivity along the length of the filaments, the filaments may also be coated or plated with materials having different or varying electrical conductivity. For example, the filaments, whether tapering or not, could be coated with conductive material. The conductive material coating the filaments in the region most closely adjacent to the distal end 24 of the outer sheath 18 may be more conductive than the coating on the portion of the filaments most closely adjacent to the distal end of the filaments themselves. Thus, the conductivity of the filaments would be greater near the distal end of the outer sheath than near the distal ends of the filaments, even though the cross-sectional areas of the filaments may not be changing substantially as one moves longitudinally along the filaments toward their distal ends. Although not specifically shown in the figures, the conductivity of all of the disclosed filaments may also vary radially rather than, or in addition to, varying longitudinally. In other words, the conductivity of the filaments may vary as one moves from the center of the filaments to the surface of the filaments.

Figure 16:
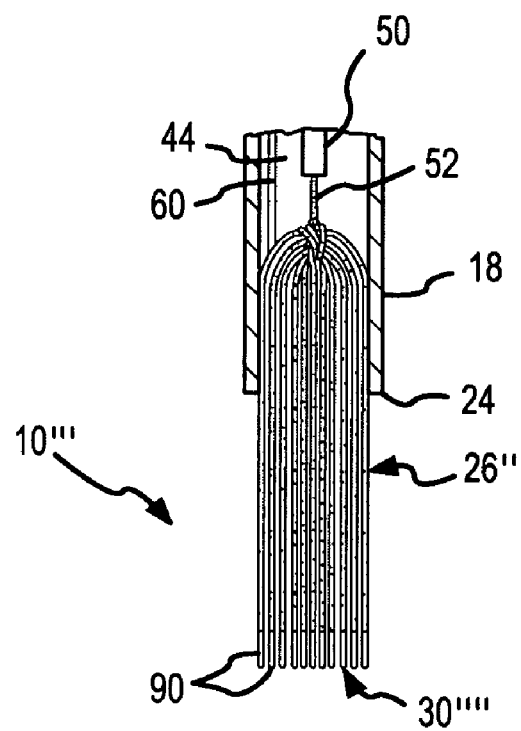
FIG. 16 depicts an alternative embodiment of the filaments comprising the brush electrode, wherein the individual filaments have nonconductive tips at their distal ends creating a stand-off distance.

FIG. 16 depicts a brush electrode 10'''' in which the conductivity of the filaments varies discontinuously. In particular, FIG. 16 depicts filaments 26'' that are conductive except at their distal ends. The distal end of each filament includes a nonconductive tip 90. These nonconductive tips provide a stand-off distance when the working surface of the brush electrode is placed substantially perpendicular to the tissue being treated since the conductive portions of the filaments do not actually touch the tissue in this embodiment. Similar to what occurs in the embodiment depicted in FIGS. 8-10, the conductive fluid would pass through the lumen of the catheter and wet the brush. The conductive fluid would carry the current over the stand-off distance and to the tissue, thereby acting as a virtual electrode. It should be noted that, although the embodiment depicted in FIG. 16 shows each of the conductive filaments 26'' having a nonconductive tip 90, some of the conductive filaments 26'' may extend all the way to the working surface 30'''' of the brush electrode and thus would, in fact, contact the tissue during use of the brush electrode.

Figure 17:
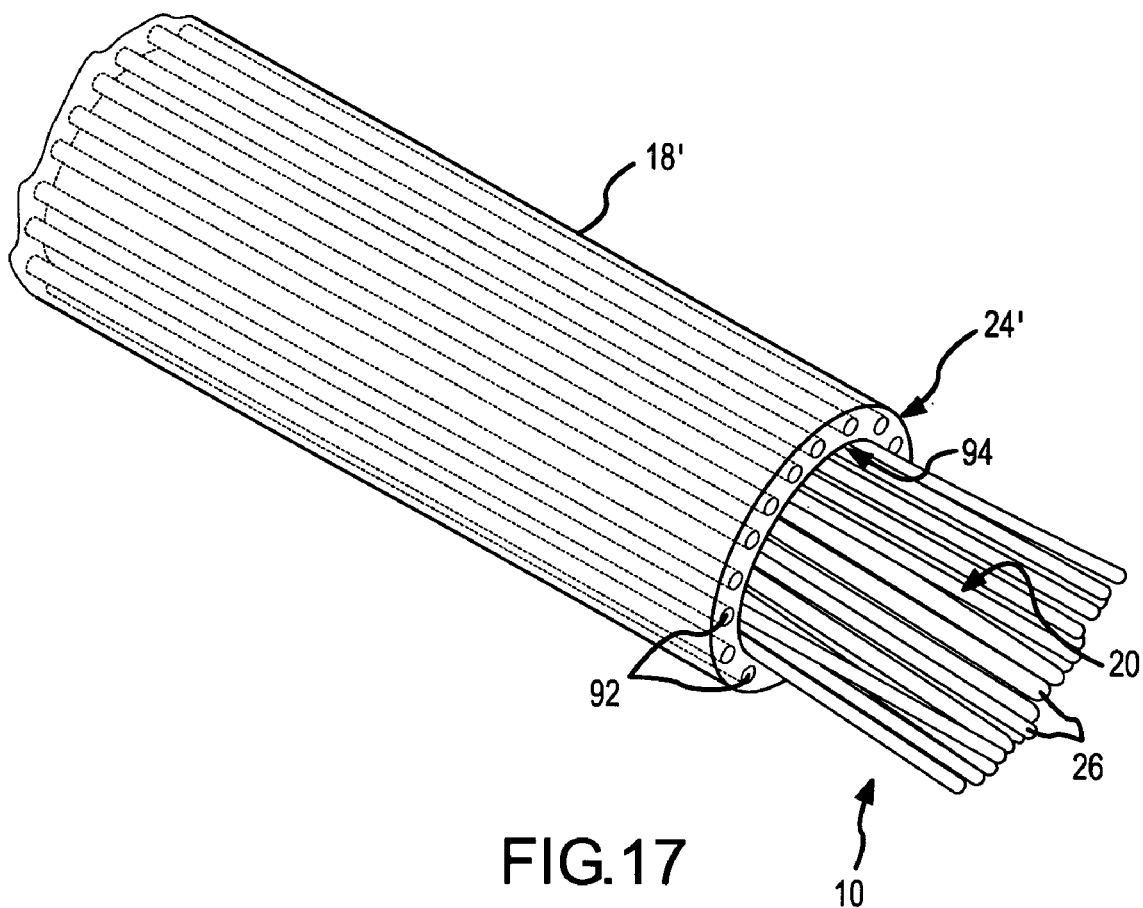
FIG. 17 is a fragmentary, isometric view of an embodiment of the outer sheath having a concentric ring of subchannels around a main or central channel through which the brush filaments extend.

FIG. 17 depicts an embodiment of the outer sheath 18' having a concentric ring of sub-channels 92 around a main or central channel 94 through which the brush filaments 26 extend. The circumferential ring of sub-channels around the brush-carrying central channel may be used to carry conductive or nonconductive fluid, including therapeutic fluid or medicine. The embedded sub-channels depicted in this figure could define spiral or helical paths toward the distal end 24' of the outer sheath, similar to the paths or channels 104 described below in connection with FIG. 19 and FIG. 20.

Figure 18:
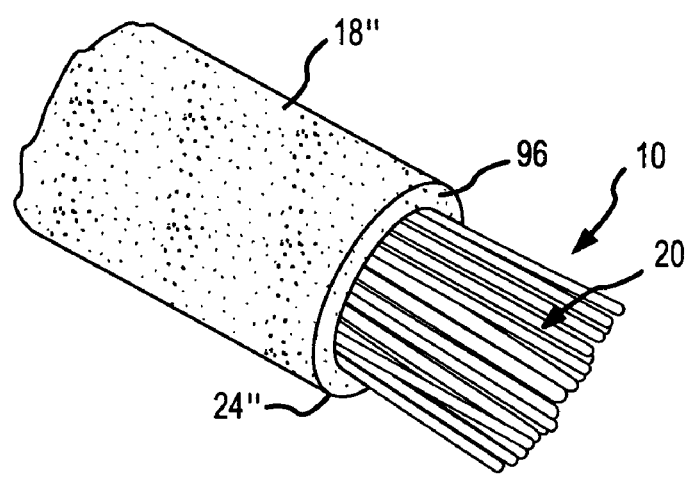
FIG. 18 is a fragmentary, isometric view of an embodiment wherein the sheath surrounding the filaments of the brush electrode is porous adjacent to the exposed portion of the brush electrode.

FIG. 18 depicts an embodiment wherein the sheath 18'' surrounding the filaments of the brush electrode 10 is porous adjacent to the exposed portion 20 of the brush electrode. An outer covering (not shown) may be placed around the outer cylindrical surface of the porous sheath, possibly leaving an angular ring of material 96 exposed at the distal end 24'' of the sheath 18'' adjacent to the brush electrode 10.

Figure 19:
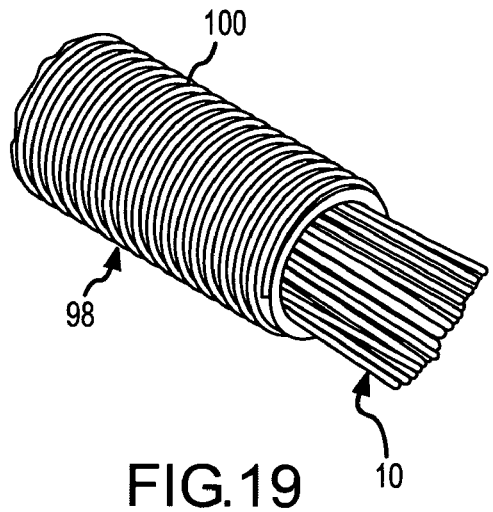
FIG. 19 is a fragmentary, isometric view of an embodiment wherein the sheath surrounding the filaments of the brush electrode is a threaded sheath, having a spiral or helical ridge on its outer surface, adjacent to the exposed portion of the brush electrode.
Figure 20:
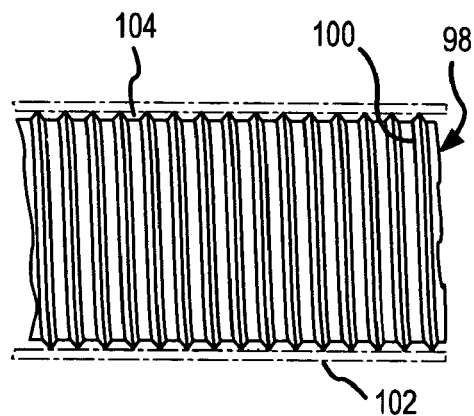
FIG. 20 is a fragmentary view of a section of the threaded sheath depicted in FIG. 19, surrounded by a covering shown in phantom and cross-section to create a helical flow channel between the threaded sheath and the covering.

FIG. 19 is a fragmentary, isometric view of an embodiment wherein a threaded sheath 98 surrounds the filaments of the brush electrode 10. The threaded sheath 98 has a spiral or helical ridge 100 on its outer surface. As shown to good advantage in FIG. 20, when the threaded sheath is inserted into a covering 102 (shown in phantom and cross-section), a helical flow channel 104 is created between the threaded sheath 98 and the covering 102. Conductive fluid, nonconductive fluid, or medication may be delivered to the tissue adjacent to the brush electrode via this flow channel.

Figure 21:
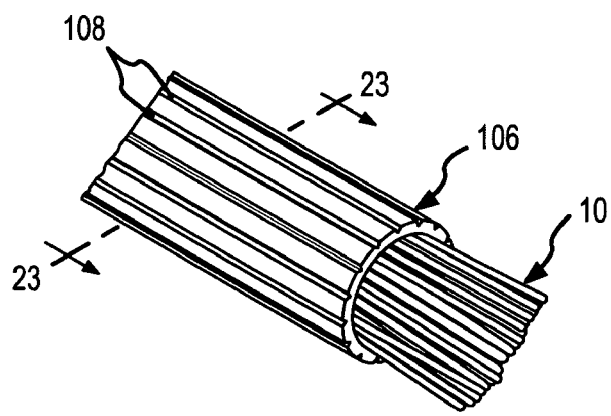
FIG. 21 is a fragmentary, isometric view of an embodiment wherein the sheath surrounding the filaments of the brush electrode is a grooved sheath, having a plurality of longitudinally-extending grooves or cuts on its outer surface, adjacent to the exposed portion of the brush electrode.
Figure 22:
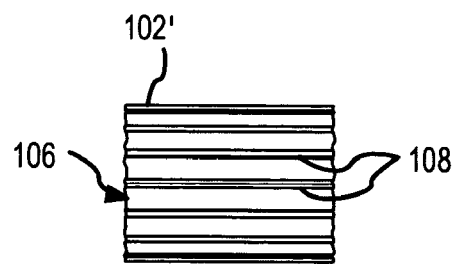
FIG. 22 is a fragmentary view of a section of the grooved sheath depicted in FIG. 21, surrounded by a covering (shown cross-section) to create a plurality of longitudinally-extending flow channels between the grooved sheath and the covering.
Figure 23:
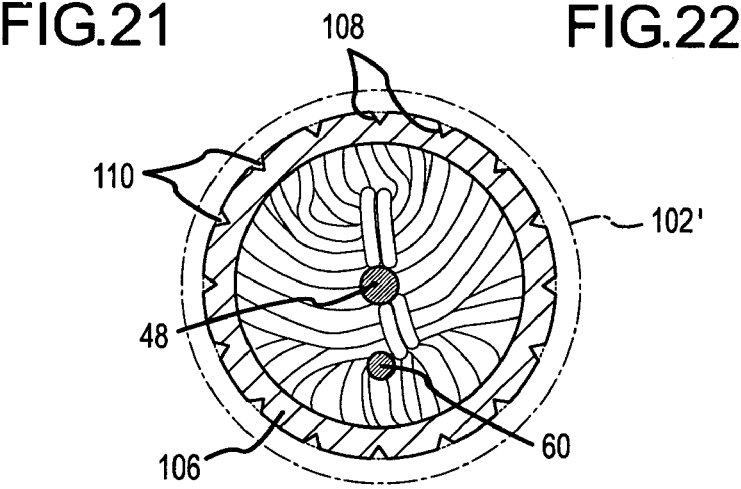
FIG. 23 is a cross-sectional view taken along line 23-23 of FIG. 21, with the covering shown in phantom and with the longitudinally-extending flow channels clearly visible.

FIG. 21 is a fragmentary, isometric view of another embodiment, wherein the sheath surrounding the filaments of the brush electrode is a grooved sheath 106. The grooved sheath has a plurality of longitudinally-extending grooves or cuts 108 formed on its outer surface, adjacent to the exposed portion of the brush electrode 10. As shown to best advantage in FIG. 23, when the grooved sheath 106 is inserted into a covering 102' (shown in phantom and cross-section), a plurality of longitudinally-extending flow channels 110 are created between the grooved sheath 106 and the covering 102'. Again, conductive fluid, nonconductive fluid, or medication may be delivered to the tissue adjacent to the brush electrode via these flow channels. FIG. 22 is a fragmentary view of a section of the grooved sheath 106 depicted in FIG. 21, surrounded by a covering 102' (shown in cross-section) to create the plurality of longitudinally-extending flow channels 110 between the grooved sheath and the covering.

Figure 24:
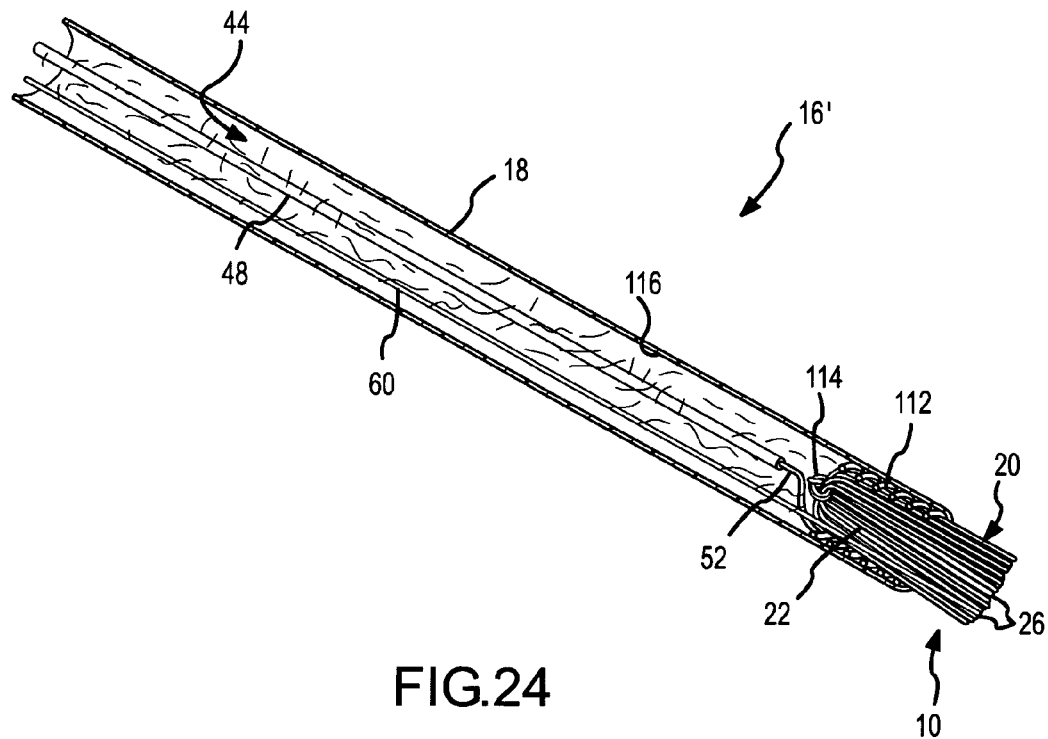
FIG. 24 is similar to FIG. 5, but depicts an isometric, cross-sectional view of a catheter wherein the primary conductor makes electrical contact with the filaments via an energy transfer coil or spring surrounding at least the embedded portion of the brush electrode.
Figure 25:
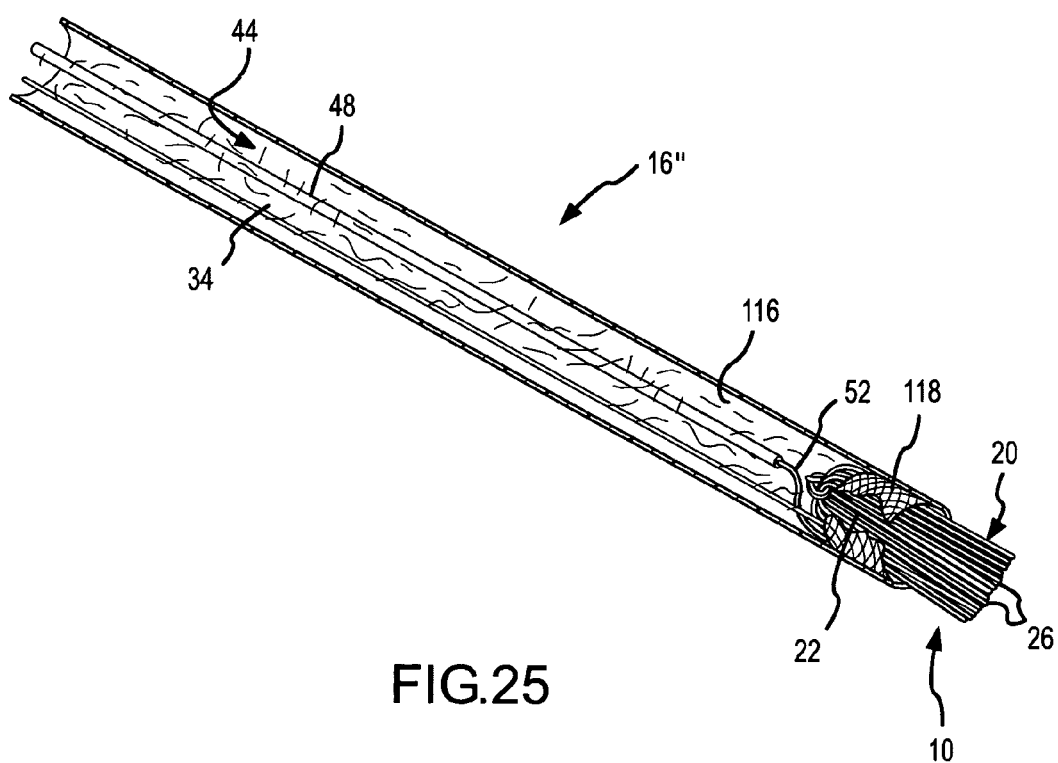
FIG. 25 is similar to FIGS. 5 and 24, but depicts an isometric, cross-sectional view of a catheter wherein the primary conductor makes electrical contact with the filaments via an energy transfer mesh or fabric surrounding at least the embedded portion of the brush electrode.

FIGS. 24 and 25 depict alternative mechanical interfaces between the filaments 26 of the brush electrode 10 and the primary conductor 48. FIG. 24 is similar to FIG. 5, but depicts an isometric, cross-sectional view of a catheter 16' wherein the exposed portion 52 of the primary conductor 48 makes electrical contact with the brush filaments 26 via an energy transfer coil or spring 112 surrounding at least the concealed or embedded portion 22 of the brush electrode 10. In this embodiment, the ablative energy is transferred to the brush electrode 10 over a large surface area (i.e., over the entire inner surface area of the coil 112). Thus, less damage to the filaments may occur in this embodiment than may occur in the embodiment depicted in FIG. 5, wherein all of the ablative energy is transferred from the uninsulated portion 52 of the primary conductor to the brush electrode at the single connection point 56. As depicted in FIG. 24, a loop of wire 114 may be present to help collect and stabilize the filaments 26 during assembly of the catheter 16'. This loop of wire 114 may be anchored to, for example, the inner surface 116 of the outer sheath 18. As previously described, a secondary lead 60 may also be present in the lumen 44 of the outer sheath 18.

FIG. 25 is similar to FIGS. 5 and 24, but depicts an isometric, cross-sectional view of a catheter 16" wherein the primary conductor 48 makes electrical contact with the filaments of the brush electrode 10 via an energy transfer mesh or fabric 118 surrounding at least the concealed or embedded portion 22 of the brush electrode 10. This embodiment has the same advantages that were just described for the embodiment depicted in FIG. 24. In another embodiment, the primary conductor 48 makes electrical contact with the filaments of the brush electrode 10 via an energy transfer wrap (not shown), which is similar to the mesh or fabric 118, but comprises a solid or porous sheet of conductive material.

Figures 26, 27:
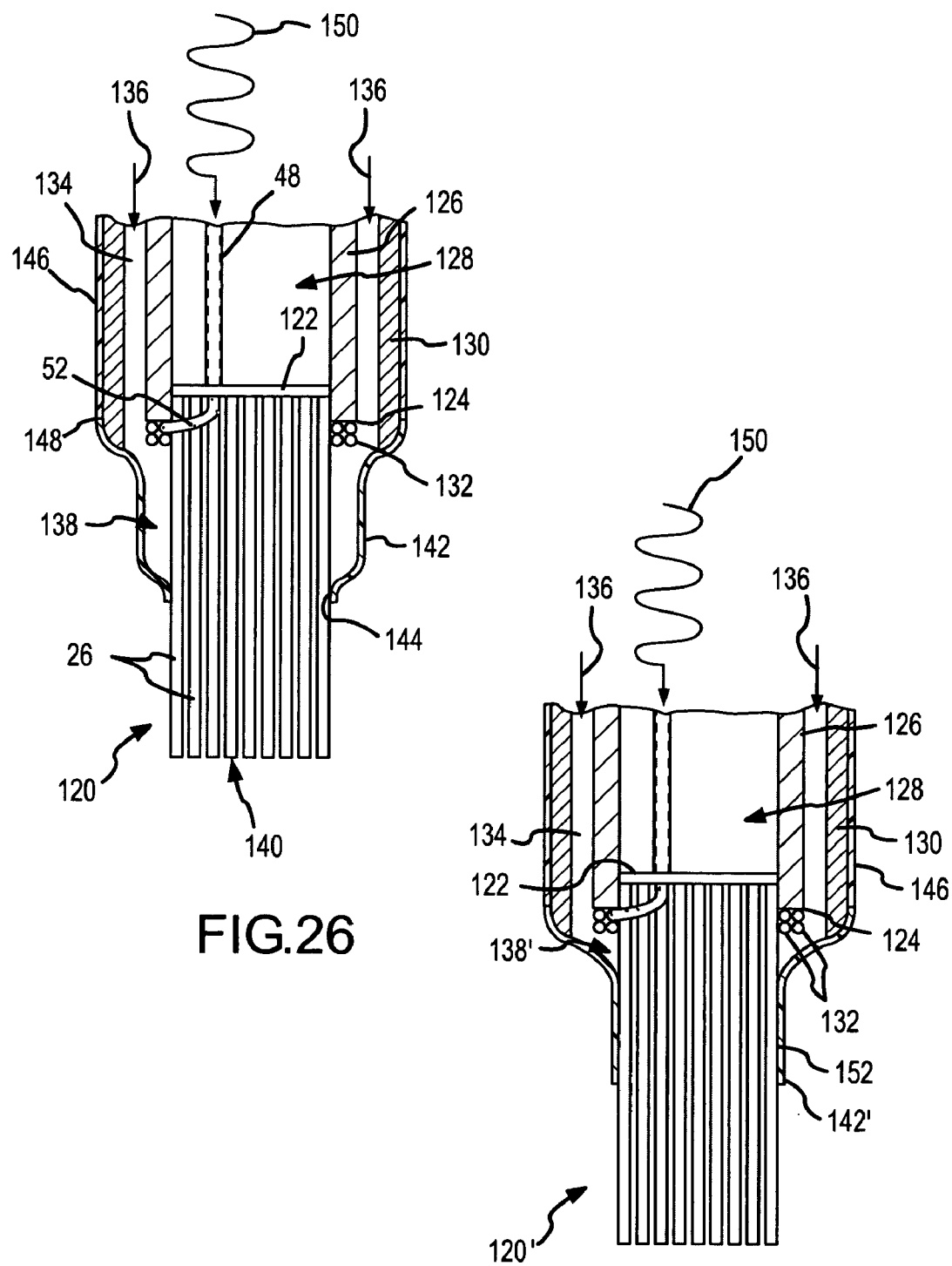
FIG. 26 is a cross-sectional view of a first embodiment of a shielded-tip brush electrode, wherein an uninsulated portion of the primary conductor is looped around the outer surface of the brush electrode.
FIG. 27 is similar to FIG. 26, but depicts a second embodiment of a shielded-tip brush electrode.

FIG. 26 is a cross-sectional view of a first embodiment of a shielded-tip brush electrode 120. In this embodiment, the uninsulated portion 52 of the primary conductor 48 is looped around the outer surface of the brush electrode after passing through a mechanical interface 122 supporting the filaments 26 of the brush electrode adjacent to the distal end 124 of an inner sheath 126. Since fluid may or may not travel through the lumen 128 of the inner sheath 126, the mechanical interface 122 may or may not be porous. In the embodiment depicted in FIG. 26, there is an outer sheath 130 surrounding the inner sheath 126. The inner sheath houses the primary conductor 48 and supports the mechanical interface 122 for the filaments 26 of the brush electrode 120. The primary conductor again includes an uninsulated portion 52 that transfers ablative energy 150 (e.g., RF energy) to the conductive filaments in the brush electrode 120. As mentioned, in this embodiment the uninsulated portion 52 of the primary conductor forms loops or coils 132 around the circumference of the brush. These loops or coils increase the surface area through which the ablative energy is transferred, thereby providing for more effective, and potentially less destructive, energy transfer to the brush electrode 120.

As shown in FIG. 26, the outer sheath, which may be a typical braided sheath, is placed around the inner sheath 126, but is radially and longitudinally offset from the inner sheath. The radial offset creates an annular gap or channel 134 between the inner sheath 126 and the outer sheath 130 through which conductive fluid may, for example, be introduced to the sides of the brush electrode filaments. The conductive fluid, if present, would flow through the annular channel 134 in the direction of the arrows 136 shown at the top of FIG. 26. The longitudinal offset between the inner sheath 126 and the outer sheath 130 ensures that the channel 134 for the conductive fluid extends past the distal end 124 of the inner sheath 126 to the sides of the brush electrode filaments. In this embodiment, the conductive fluid would flow through the annular channel between the inner sheath and the outer sheath, past the coils 132 of uninsulated conductive wire, into an annular fluid jacket 138 surrounding a region of the brush electrode adjacent to the distal ends of the inner and outer sheaths, and then into the sides of the brush electrode itself and through the interstitial gaps between the filaments comprising the brush electrode. The ablative energy (e.g., the RF energy 150) is thus carried by the conductive fluid into the core of the brush electrode and toward its working surface 140. In this embodiment, a flexible polymer nipple or boot 142, defining an outer wall of the annular fluid jacket 138, also supports the filaments in a ring 144 of direct contact extending around the perimeter of the filament bundle. The flexible boot or nipple may be porous. Finally, a smooth outer wall 146 to facilitate easier insertion and manipulation of the catheter in a patient may cover the outer sheath 130 and abut a corresponding edge 148 of the flexible polymer nipple or boot 142. Alternatively, the outer wall material may actually form the nipple or boot in addition to forming a perimetric covering around the outer sheath. An annular layer of porous material or mesh fabric (not shown) may be placed in the annular fluid jacket 138 to keep the brush wetted and to help prevent splaying (see FIGS. 40-42) of the brush electrode.

FIG. 27 is similar to FIG. 26, but depicts a second embodiment of a shielded tip brush electrode 120'. The only differences between the embodiment depicted in FIG. 26 and the embodiment depicted in FIG. 27 are the size of the fluid jacket 138' and the configuration of the flexible polymer nipple or boot 142' that supports the brush filaments. In the embodiment depicted in FIG. 27, an alternative flexible polymer nipple or boot 142' defines a smaller fluid jacket 138' and supports the filaments in a band of direct contact extending around the perimeter of the filament bundle. The band of direct contact 152 supports the filaments over a larger section of the outer surface of the brush electrode than does the ring of direct contact 144 depicted in FIG. 26. By adjusting the configuration of the flexible polymer nipple or boot in this manner, the amount of conductive fluid flowing into the brush electrode and the overall flexibility of the brush electrode can be manipulated.

It should be noted that, although the filaments depicted in FIGS. 26 and 27 are shown as extending just into the distal end 124 of the inner sheath 126, the filaments may extend further into the inner sheath and may even extend all the way to the proximal end (not shown) of the catheter.

FIGS. 28-35 depict different cross-sectional configurations for brush electrodes according to the present invention. Interstitial spaces 156 are clearly visible in each of these figures. In FIGS. 28-31, the brush electrode 10 has a conductive core 154. In these four figures, the conductive filaments 72 are shown with cross hatching, and the nonconductive filaments 74 are shown without cross hatching. Thus, the brush electrode depicted in FIG. 28 is fully conductive and does not comprise any nonconductive filaments. In each of the embodiments depicted in FIGS. 29-31, a conductive core 154 is shielded by a barrier of nonconductive filaments 74. In particular, FIG. 29 depicts a core of relatively large conductive filaments surrounded by two rings of nonconductive filaments of approximately the same size. In FIG. 30, a core 154 of relatively small conductive filaments 72 is surrounded by two rings of relatively large nonconductive filaments 74. In FIG. 31, a conductive core 154 of relatively large conductive filaments 72 is surrounded by two rings of relatively small nonconductive filaments 74.

Figure 32:
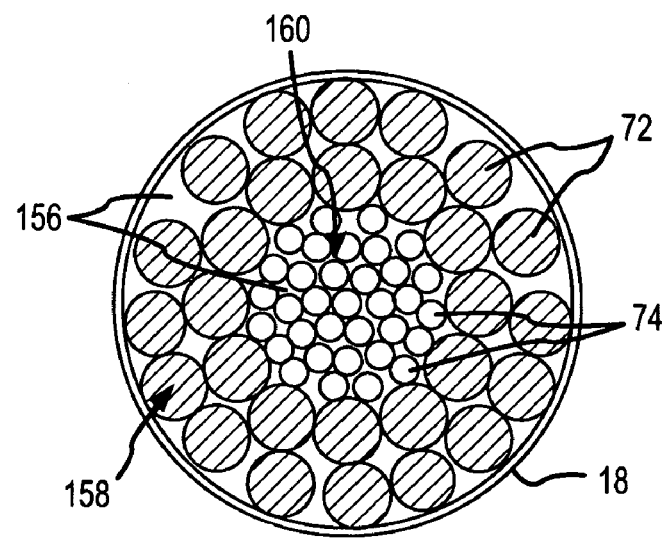
Figure 33:
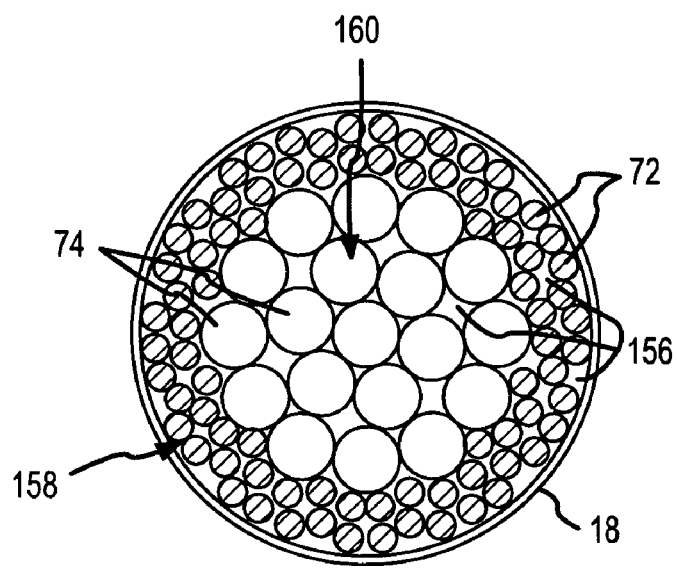

FIGS. 32 and 33 depict cross-sectional configurations for brush electrodes that have conductive perimeters 158. Thus, in the embodiments depicted in FIGS. 32 and 33, a nonconductive core 160 of nonconductive filaments 74 is surrounded by conductive filaments 72. FIG. 32 depicts a core of relatively small nonconductive filaments surrounded by two rings of relatively large conductive filaments. In FIG. 33, a core of relatively large nonconductive filaments is surrounded by two rings of relatively small conductive filaments.

Figure 34:
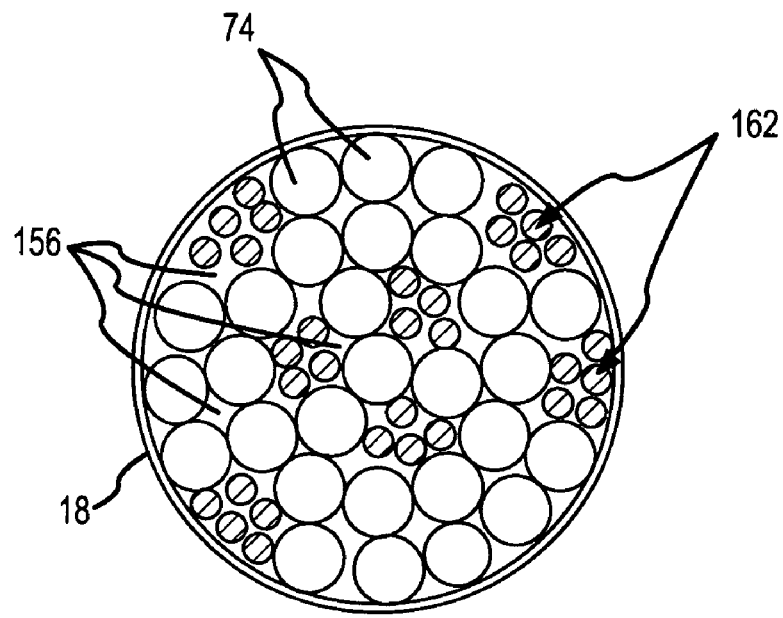
Figure 35:
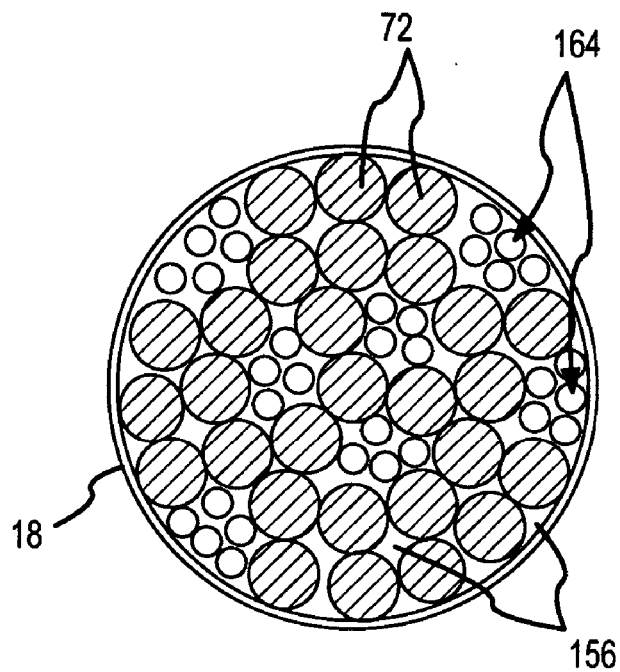

In FIG. 34, conductive clusters 162 of relatively small filaments are interspersed among relatively large nonconductive filaments 74. The interspersed conductive clusters may be interspersed in a specific pattern, pseudo randomly, or randomly among the nonconductive filaments in order to achieve a desired electric field from the resulting brush electrode. In FIG. 35, nonconductive clusters 164 of relatively small filaments are interspersed among relatively large conductive filaments 72.

Figure 36:
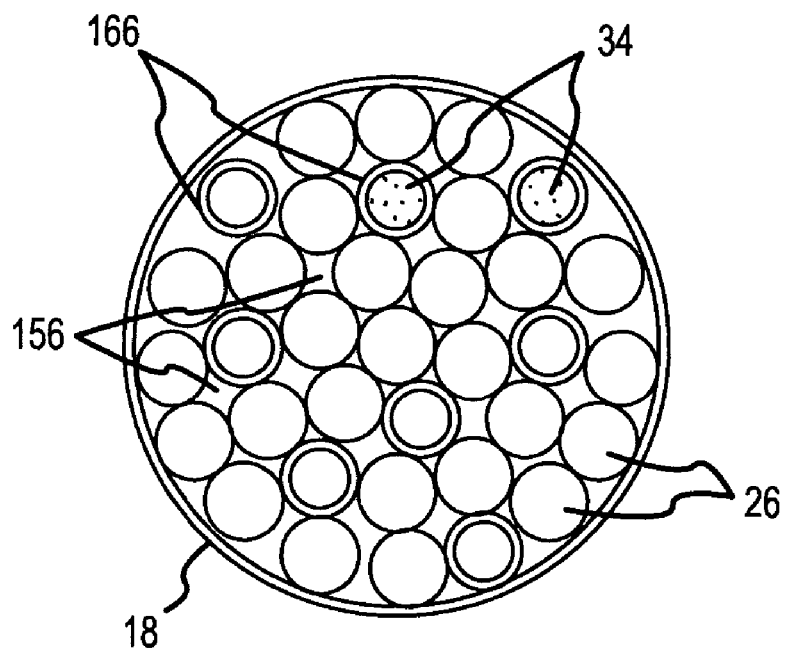
FIG. 36 is a cross-sectional view of a brush electrode wherein some of the filaments comprise hollow or porous members.

FIG. 36 is a cross-sectional view of a brush electrode wherein some of the filaments are hollow or porous 166. Such hollow or porous filaments 166 may be used as conduits for conductive fluid, they may be used to supply therapeutic chemicals, and/or they may provide suction ports at the brush-tissue interface to control field smearing on the tissue surface. If the filaments are porous, they may retain a small amount of fluid in pores that are oriented at various angles to the longitudinal axis of the filaments. During an ablation procedure, some of the ablative energy may dehydrate the porous filaments before affecting the surrounding blood, particularly when the conductivity of the tissue lessens as the ablation progresses. Thus, if excess ablative energy is present during an ablation procedure, that energy may harmlessly dehydrate the porous filaments rather than negatively affecting the tissue being ablated or the blood in the area of that tissue. In one embodiment (not shown), some of these hollow filaments 166 do not extend to the distal end 32 (labeled on, for example, FIG. 2) of the brush electrode. For example, some of the hollow filaments 166 may only extend part way into the exposed portion 20 (labeled on, for example, FIG. 3) of the brush electrode. These shortened hollow filaments may deliver conductive fluid or therapeutic chemicals, for example, to an interior region of the bundle of brush filaments. In the embodiment depicted in FIG. 36, the other filaments 26 may be conductive or nonconductive filaments.

Figure 37:
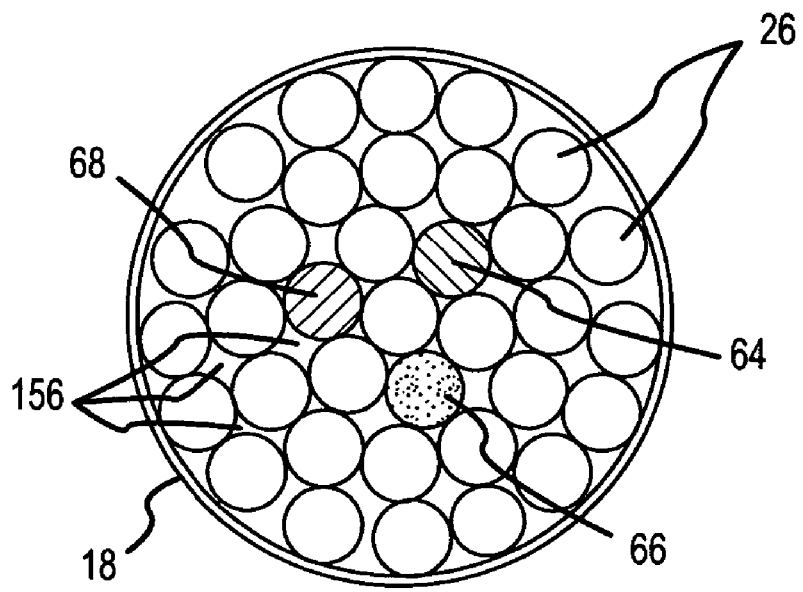
FIG. 37 is a cross-sectional view of a brush electrode having devices (e.g., a thermocouple or other temperature sensor, a pressure sensor, or an ultrasound sensor) embedded among the conductive and nonconductive filaments.

FIG. 37 is a cross sectional view of a brush electrode having devices 64, 66, 68 embedded among the conductive and nonconductive filaments 26. The devices may include, for example, pressure sensors 68 to measure contact pressure between the brush electrode and the tissue, thermal sensors 64 (e.g., a thermocouple) at the tip of the brush electrode to sense the brush-tissue interface temperature, or fiber optic or ultrasound sensors 66 for in situ lesion identification and characterization. The devices may be operatively connected to equipment (not shown) at the proximal end of the catheter by secondary leads like the secondary lead 60 depicted in, for example, FIGS. 5 and 8-16.

Figure 38:
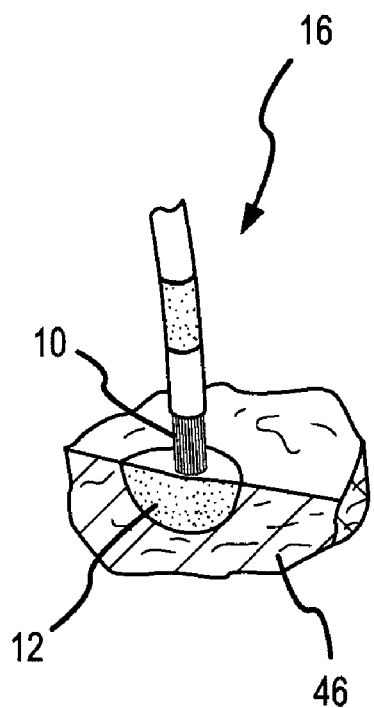
FIG. 38 is an isometric view of a catheter having a brush electrode according to the present invention forming a spot or point lesion on a section of tissue.
Figure 39:
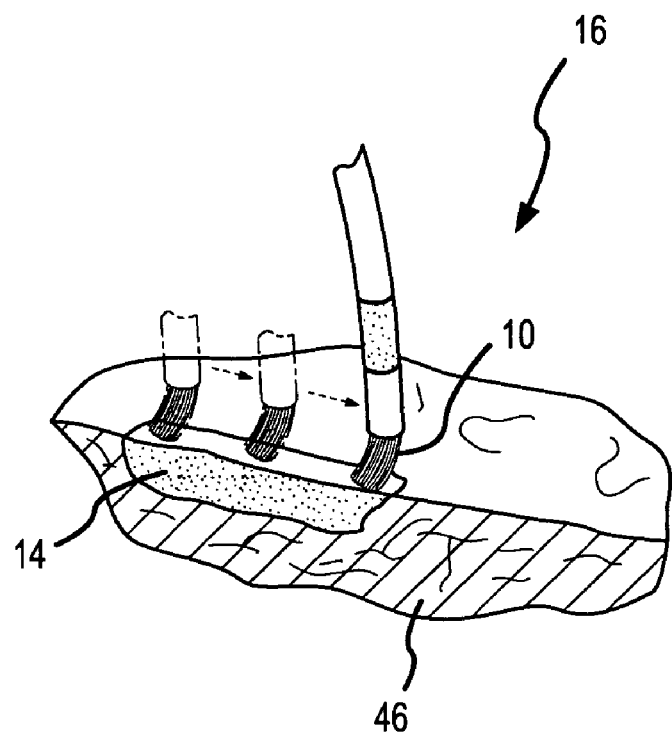
FIG. 39 is an isometric view of a catheter having a brush electrode according to the present invention forming a linear or drag lesion on a section of tissue.

FIG. 38 is a fragmentary, isometric view of a catheter 16 having a brush electrode 10 according to the present invention forming a spot or point lesion 12 on a section of tissue 46. As shown in this figure, the brush electrode is placed against the tissue with its filaments in contact with or in close proximity to the tissue. The conductive filaments are connected to, for example, an RF source (not shown) and serve as the active electrode. When present, conductive fluid from a fluid source (not shown) flows through the lumen 44 (e.g., FIG. 5) of the catheter and through the brush filaments to the working surface at the brush tip, thereby creating a wet-brush electrode. Rather than being localized on the tissue to create a spot or point lesion 12 as shown in FIG. 38, the brush electrode 10 may be dragged along the surface of the tissue 46 to create a continuous linear lesion 14, as shown in FIG. 39. FIG. 39 is a fragmentary, isometric view of a catheter 16 having a brush electrode according to the present invention forming a linear or drag lesion on a section of tissue.

Figure 40:
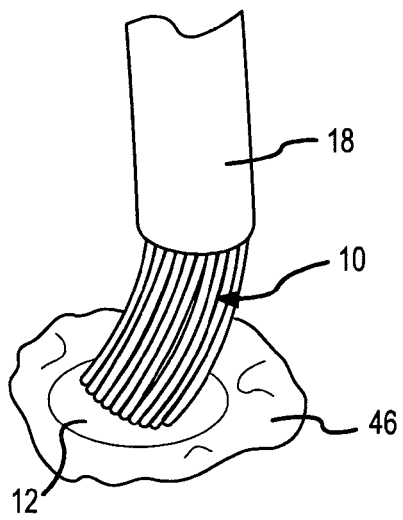
FIGS. 40-42 depict a brush electrode according to the present invention forming different-sized lesions based in part upon the amount of splay of the brush electrode.
Figure 41:
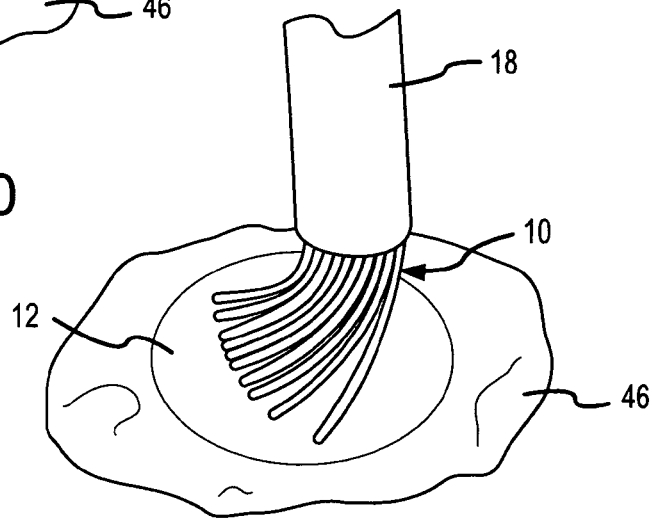
Figure 42:
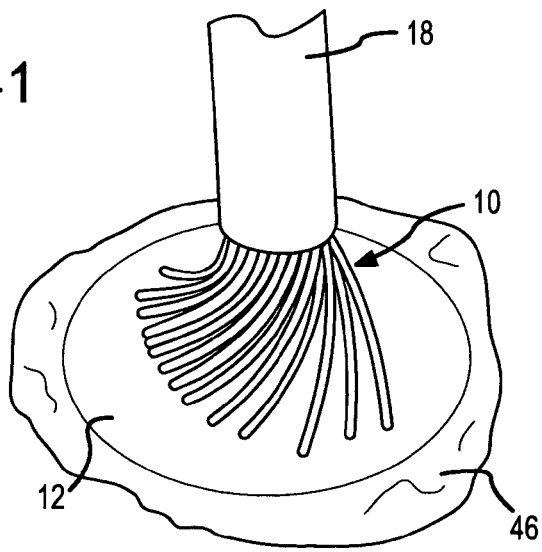

FIGS. 40-42 depict a brush electrode 10 according to the present invention forming different size spot lesions 12 based in part upon the amount of splay of the brush electrode. In FIG. 40, relatively light contact pressure is being used to press the brush electrode 10 against the tissue 46 while forming a lesion 12. This application of light pressure results in minimal splaying of the filaments comprising the brush electrode, and thus a relatively small lesion is formed. In FIG. 41, more pressure is being used to press the brush electrode 10 into contact with the tissue 46, resulting in relatively more splaying of the brush electrode. As long as the efficiency of the brush electrode is not degraded too greatly by the splaying, a relatively larger lesion 12 may thus be formed by applying additional pressure to press the brush electrode toward the tissue. Finally, in FIG. 42, even more contact pressure is being applied to the brush electrode 10 than is being applied in FIGS. 40 and 41, resulting in even more splaying of the brush electrode and the formation of a relatively larger lesion 12 on the tissue 46 than is being formed in FIGS. 40 and 41.

The brush electrode according to the present invention delivers ablative energy to the tissue via the conductive filaments alone, via the conductive fluid alone, or via both the conductive filaments and the conductive fluid. In the latter two configurations, the brush electrode is referred to as a wet-brush electrode. Since it is possible for the conductive fluid to escape from the exposed portion of the wet-brush electrode prior to reaching the working surface at the distal tip of the wet-brush electrode, there is some ablative energy leakage to the surrounding blood. The leakage of ablative energy to the surrounding blood is in part due to direct contact between the blood and the conductive filaments and in part due to the conductive fluid escaping between the filaments to the surrounding blood, particularly when substantial splaying of the filaments occurs (see, e.g., FIG. 42).

The design parameters for the brush electrode include both filament and brush parameters. The filament parameters include, for example, the material and structural properties of the individual filaments (e.g., what material(s) each individual filament is constructed from, whether the filaments are hollow or solid, whether the filaments are porous, and how flexible or stiff the filaments are), the shape and cross-sectional areas of the individual filaments, and the electrical conductivity of the individual filaments. The electrical conductivity of the individual filaments may be constant along the length of the filaments or may vary along the length of the filaments. Also, if the conductivity of a filament varies along its length, it may vary continuously or discontinuously. The filament design parameters may be different for each filament.

The design parameters for the brush electrode include, for example, the overall shape and cross-sectional area of the brush (i.e., the overall shape and size of the filament bundle forming the brush electrode), the tip length of the brush itself (i.e., the length of the portions of the filaments that extend the farthest from the distal end of the outer sheath), the shape of the brush tip, the length of the individual filaments relative to each other, the packing density of the filaments comprising the brush, and the overall electrical resistance of the brush. When both nonconductive and conductive filaments are present, the conductive filaments may be distributed evenly, randomly, or pseudo-randomly among the nonconductive filaments comprising the brush electrode.

By controlling, among other things, the cross-sectional shapes of the filaments, the cross-sectional areas of the filaments, the flexibility or stiffness of the filaments, the packing density of the filaments, the ratio of the nonconductive filaments to the conductive filaments, and the placement of the nonconductive and conductive filaments relative to each other, it is possible to obtain brush electrodes having desired electrical and thermal characteristics, which ultimately determine the types of lesions that may be obtained when using the brush electrodes for ablation. As mentioned above, it is even possible to vary the mechanical and electrical properties of each individual filament, if necessary, to achieve desired results.

The shapes and cross-sectional areas of the individual filaments and the packing density of the brush electrode affect the interstitial spaces between the filaments. The interstitial spaces between the filaments determine the flow path of the conductive or nonconductive fluid when the brush electrode is being used as a wet-brush electrode. The flow path of the conductive or nonconductive fluid determines to a great extent the electrical and thermal characteristics of the wet-brush electrode. The use of a large number of individual filaments defining interstitial spaces among the filaments results in efficient and effective cooling of the brush electrode and of the tissue surface. The effective cooling of the brush electrode achieved by the present invention reduces the formation of coagulum on the electrode, and the effective cooling of the tissue surface achieved by the present invention allows for the application of high-power ablation energy for long durations, ultimately resulting in the formation of better lesions.

During use of a brush electrode, the following operating parameters may be taken into account: the incidence angle between the brush electrode and the tissue, the stand-off distance between the brush electrode and the tissue, the power being applied, the rate of fluid flow when present, and the duration of contact between the electrode and the tissue.

In one set of tests, Thunderon® filaments were used favorably in a wet-brush electrode having a circular cross section with an overall diameter of 6-8 French, a tip length of 2-3 millimeters, and electrical resistance of 100-150 ohms. In this embodiment, the size of the Thunderon® filaments was 40 decitex. When using this brush electrode with zero stand-off distance, 30 watts of power, saline flowing at 12 milliliters per minute, and contact between the wet-brush electrode and the tissue occurring for 60 seconds, 5-to-6 millimeter deep lesions were formed with an incidence angle of 90° between the wet-brush electrode and the tissue. Four millimeter deep lesions were formed when the incidence angle between the wet-brush electrode and the tissue was 0°. When a stand-off distance of 1 millimeter was used during tests with similar operating parameters, a slightly less deep (on the order of 3 millimeters deep) lesion was formed.

In another set of tests, lesions 3-13 millimeters deep were created using 20-50 watts of power and flow rates of 3-18 milliliters per minute with wet-brush electrodes made from commercially available carbon fibers (e.g., carbon fibers available through Cytec Carbon Fibers LLC of South Carolina, United States of America. Isotonic saline infusion was used in these tests. Isotonic saline is generally about twice as conductive as the surrounding blood. In other tests, linear lesions 20-42 millimeters long and 3-8 millimeters deep were created by applying 20-50 watts of power for 60 seconds in the presence of flow rates of 3-18 milliliters per minute using wet-brush electrodes produced with conductive filaments made from Thunderon®.

As already mentioned, when conductive fluid is used, the brush electrode becomes a wet-brush electrode. In a wet-brush electrode, the conductive fluid serves both thermodynamic functions and electrical functions. Thermodynamically, the conductive fluid cools both the electrode and the tissue surface. As previously mentioned, effective cooling of the electrode inhibits or prevents coagulum formation on the electrode; and effective cooling of the tissue surface permits longer application of relatively high ablative energy, resulting in the formation of the deeper lesions. Electrically, the conductive fluid serves as a virtual electrode. The conductive fluid also insulates the conductive brush filaments from the surrounding blood, which helps prevent the formation of coagulum. The conductive fluid also creates a conductivity gradient resulting from a concentration gradient. The conductive fluid flowing through the brush interstitium has a field homogenizing effect. The conductive fluid flowing through the working surface at the distal tip of the wet-brush electrode thus helps to mitigate hot spots resulting from edge effects. Further, since the number of edges present in a brush electrode greatly exceeds the number of edges present in many existing electrodes, the energy build up at each filament edge in a brush electrode is less than it would be for existing electrodes, assuming the same power setting. This results in less severe edge effects when using the brush electrode of the present invention. The conductive fluid, when used, further smoothes or reduces the undesirable edge effects.

In the wet-brush electrode, the filaments serve both mechanical and electrical functions. Mechanically, the filaments create a flexible electrode that provides improved tissue contact. The filaments also create interstitial spaces, which not only provide effective fluid channeling, but also prevents the "virtual electrode" from being washed away by the surrounding blood, and helps to smooth the concentration gradient of the conductive fluid. Electrically, the filaments serve as a conductive electrode.

Again, it should be noted that although the filaments are depicted in nearly all of the figures as having circular cross-sections for visual simplicity, the individual filaments may intentionally or unintentionally have a wide variety of cross-sectional configurations and areas, and need not be circular. Manufacturing irregularities may result in various cross-sectional configurations, or filaments having a variety of different cross-sectional configurations may be intentionally selected to achieve a desired electric field at the brush-tissue interface. The filaments also may not be perfectly aligned longitudinally. Further, the filaments may comprise a yarn of braided or twisted groups of fibers, or the filaments may comprise a roving pattern of untwisted, longitudinally-extending, substantially-parallel, conductive and nonconductive fibers.

Although several embodiments of this invention have been described above with a certain degree of particularity, those skilled in the art could make numerous alterations to the disclosed embodiments without departing from the spirit or scope of this invention. All directional references are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter, the catheter comprising
   an outer sheath having a distal end;
   an inner sheath having a distal end;
   an annular channel defined between said outer sheath and said inner sheath, wherein said annular channel is adapted to carry fluid;
   a mechanical interface supported at least in part by said distal end of said inner sheath;
   a flexible electrode adapted to apply ablative energy to target tissue, wherein said flexible electrode is supported by said mechanical interface, wherein said flexible electrode comprises an embedded portion and an exposed portion, and wherein said exposed portion extends from said distal end of said outer sheath and comprises a working surface;
   a primary conductor adapted to carry ablative energy from an energy source to said flexible electrode, wherein said primary conductor comprises an uninsulated portion in electrical contact with said flexible electrode; and
   a flexible boot at said distal end of said outer sheath, said flexible boot defining an annular fluid jacket around a booted portion of said flexible electrode, wherein said booted portion comprises at least a portion of said exposed portion of said flexible electrode, and wherein said annular fluid jacket is adapted to carry fluid that is in fluid communication with said annular channel, and said booted portion directly contacting the flexible electrode to direct the fluid to the flexible electrode.

2. The catheter of claim 1, wherein said inner sheath further comprises a lumen adapted to carry fluid, and wherein said mechanical interface is porous.

3. The catheter of claim 1, wherein said flexible electrode comprises a plurality of filaments defining a brush electrode having interstitial gaps between said filaments, wherein said interstitial gaps are adapted to direct fluid toward said working surface.

4. The catheter of claim 3, wherein said brush electrodes comprises a conductive core.

5. The catheter of claim 4, wherein said conductive core is circumscribed by nonconductive filaments.

6. The catheter of claim 3, wherein said brush electrodes comprises a nonconductive core.

7. The catheter of claim 6, wherein said nonconductive core is circumscribed by conductive filaments.

8. The catheter of claim 1, wherein said flexible boot is porous.

9. The catheter of claim 1, wherein said uninsulated portion of said primary conductor is looped around said booted portion of said flexible electrode.

10. The catheter of claim 1, wherein said uninsulated portion of said primary conductor is looped around a portion of said conforming electrode that is present in at least one of said annular channel and said annular fluid jacket.

11. The catheter of claim 1, wherein said outer sheath circumscribes said inner sheath, forming said annular channel between said inner sheath and said outer sheath, and wherein said annular channel is adapted to introduce fluid to said booted portion of said flexible electrode.

12. The catheter of claim 1, wherein said catheter further comprises a smooth outer wall covering said outer sheath.

13. The catheter of claim 1 further comprising an annular layer of porous material within said annular fluid jacket.

14. The catheter of claim 1, wherein said brush electrodes comprises conductive filaments interspersed among nonconductive filaments, the non-conductive filaments having a greater length than the conductive filaments.

15. The catheter of claim 14, wherein said conductive filaments are grouped in clusters.

16. The catheter of claim 1, wherein said flexible electrode comprises a plurality of individual hollow filaments.

17. The catheter of claim 16, wherein said plurality of individual hollow filaments comprises at least one shortened hollow filament that extends part way into said flexible electrode, and wherein said at least one shortened hollow filaments is thereby adapted to deliver fluid to an interior region of said flexible electrode.

18. The catheter of claim 1, wherein said flexible electrode comprises a plurality of individual porous filaments.

* * * * *